(12) United States Patent
Deluca et al.

(10) Patent No.: US 8,058,265 B2
(45) Date of Patent: Nov. 15, 2011

(54) 1A-HYDROXY-2-(3'-HYDROXY-PROPYLIDENE)-19-NOR-VITAMIN D COMPOUNDS AND METHODS OF MAKING AND TREATMENT THEREOF

(75) Inventors: Hector F. Deluca, Deerfield, WI (US); Rafal R. Sicinski, Warsaw (PL); Lori A. Plum, Arena, WI (US); Margaret Clagett-Dame, Deerfield, WI (US); Agnieszka Glebocka, Warsaw (PL)

(73) Assignee: Wisconsin Alumni Research Foundation, Madison, WI (US)

( * ) Notice: Subject to any disclaimer, the term of this patent is extended or adjusted under 35 U.S.C. 154(b) by 240 days.

(21) Appl. No.: 11/732,924

(22) Filed: Apr. 5, 2007

(65) Prior Publication Data
US 2007/0244072 A1  Oct. 18, 2007

Related U.S. Application Data

(60) Provisional application No. 60/789,303, filed on Apr. 5, 2006.

(51) Int. Cl.
*A61K 31/59* (2006.01)
*C07C 401/00* (2006.01)
(52) U.S. Cl. .................................. 514/167; 552/653
(58) Field of Classification Search ........... 514/167; 552/653
See application file for complete search history.

(56) References Cited

U.S. PATENT DOCUMENTS

| | | | |
|---|---|---|---|
| 4,666,634 A | 5/1987 | Miyamoto et al. | |
| 5,086,191 A | 2/1992 | DeLuca et al. | |
| 5,237,110 A | 8/1993 | DeLuca et al. | |
| 5,246,925 A | 9/1993 | DeLuca et al. | |
| 5,536,713 A | 7/1996 | Deluca et al. | |
| 5,587,497 A | 12/1996 | DeLuca et al. | |
| 5,817,648 A | 10/1998 | Kutner et al. | |
| 5,843,927 A | 12/1998 | DeLuca et al. | |
| 5,843,928 A | 12/1998 | Deluca et al. | |
| 5,877,168 A | 3/1999 | Miyamoto et al. | |
| 5,936,133 A | 8/1999 | Deluca et al. | |
| 5,945,410 A | 8/1999 | DeLuca et al. | |
| 6,392,071 B1 | 5/2002 | DeLuca et al. | |
| 6,537,981 B2 | 3/2003 | DeLuca et al. | |
| 6,806,262 B2 | 10/2004 | DeLuca et al. | |
| 6,846,811 B2 | 1/2005 | DeLuca et al. | |
| 6,992,074 B2 | 1/2006 | DeLuca et al. | |

(Continued)

FOREIGN PATENT DOCUMENTS
EP       0078704       4/1987

(Continued)

OTHER PUBLICATIONS

Jimenez, J.J., et al., "Treatment with ImuVert/N-Acetylcysteine Protects Rats from Cyclophosphamide/Cytarabine-Induced ...," Cancer Investigation 10:271-276(1992).

(Continued)

*Primary Examiner* — Sabiha Qazi
(74) *Attorney, Agent, or Firm* — Foley & Lardner LLP

(57) ABSTRACT

Disclosed are 1α-hydroxy-2-(3'-hydroxypropylidene)-19-nor-vitamin D compounds, pharmaceutical compositions, and methods of making and treatment thereof. The compounds are generally directed to biologically active 2-alkylidene-19-nor-vitamin D compounds and analogs thereof characterized by the presence of a 3'-hydroxypropylidene moiety at C-2 and the presence of an abbreviated alkyl side-chain free of any hydroxyl moiety.

28 Claims, 10 Drawing Sheets

HL-60 Cell Differentiation

- 1,25(OH)$_2$D$_3$
- RBH (8a)
- SBH (8b)

EC$_{50}$:  1,25(OH)$_2$D$_3$ = 1.4 x 10$^{-9}$ M
RBH = 5.5 x 10$^{-9}$ M (8a)
SBH = 3.6 x 10$^{-9}$ M (8b)

U.S. PATENT DOCUMENTS

| | | | |
|---|---|---|---|
| 7,541,348 | B2 | 6/2009 | DeLuca et al. |
| 2004/0229851 | A1 | 11/2004 | DeLuca et al. |
| 2005/0119242 | A1 | 6/2005 | DeLuca et al. |
| 2006/0135799 | A1 | 6/2006 | DeLuca et al. |

FOREIGN PATENT DOCUMENTS

| | | |
|---|---|---|
| EP | 0184206 | 4/1989 |
| EP | 0387077 | 1/1994 |
| EP | 0480572 | 6/1995 |
| EP | 0516410 | 7/1998 |
| EP | 0474517 | 11/1998 |
| EP | 1524264 | 4/2005 |
| JP | 6041059 | 2/1994 |
| WO | WO 90/09991 | 9/1990 |
| WO | WO 01/92221 | 12/2001 |
| WO | WO 2004/092118 | 10/2004 |
| WO | WO 2004/092118 A2 | 10/2004 |
| WO | WO 2005/051323 | 6/2005 |
| WO | WO 2006/057913 | 6/2006 |
| WO | WO 2006/057914 | 6/2006 |
| WO | WO 2007/117563 | 10/2007 |

OTHER PUBLICATIONS

Sredni, B., et al., "The Protective Role of the Immunomodulator AS101 Against Chemotherapy-Induced Alopecia Studies on Human . . . ," Int. J. Cancer 65:97-103 (1996).

Xia, C., et al., "The organization of the human GSTP1-1 gene promoter and its response to retinoic acid and cellular redox status," Biochem. J. 313:155-161 (1996).

Arbour, Nancy C. et al., "A Highly Sensitive Method for Large-Scale Measurements of 1,25-Dihydroxyvitamin D," Analytical Biochemistry, 1998, vol. 255, pp. 148-154.

Arbour, Nancy C. et al., "*TLR4* mutations are associated with endotoxin hyporesponsiveness in humans," Nature Genetics, Jun. 2000, vol. 25, pp. 187-191.

Baggiolini, Enrico G. et al., "Stereocontrolled Total Synthesis of 1α,25-Dihydroxycholecalciferol and 1α,25-Dihydroxyergocalciferol," J. Org. Chem., 1986, vol. 51, pp. 3098-3108.

Bouillon, Roger et al., "Biological Activity of Dihydroxylated 19-Nor-(Pre) Vitamin $D_3$," Journal of Bone and Mineral Research, 1993, vol. 8, No. 8, pp. 1009-1015.

Collins, S. J. et al., "Normal Functional Characteristics of Cultured Human Promyelocytic Leukemia Cells (HL-60) After Induction of Differentiation by Dimethylsulfoxide," J. Exp. Med., 1979, vol. 149, pp. 969-974.

Dame, Margaret C. et al., "Monoclonal Antibodies to the Porcine Intestinal Receptor for 1,25-Dihydroxyvitamin $D_3$: Interaction with Distinct Receptor Domains," Biochemistry, 1986, vol. 25, pp. 4523-4534.

Fall, Yagamare et al., "Vitamin D heterocyclic analogues. Part 1: A stereoselective route to CD systems with pyrazole rings in their side chains," Tetrahedron Letters, 2002, No. 43, pp. 1433-1436.

Fujishima, Toshie et al., "Synthesis and Biological Activity of 2-Methyl-20-EPI Analogues of 1α,25-Dihydroxyvitamin $D_3$," Bioorganic & Medicinal Chemistry Letters, 1998, vol. 8, pp. 2145-2148.

Glebocka, Agnieszka et al., "New derivative of 1α,25-dihydroxy-19-norvitamin $D_3$ with 3'-alkoxypropylidene moiety at C-2: synthesis, biological activity and conformational analysis," J. Steroid Biochem. Mol. Biol., 2004, vol. 89-90, pp. 25-30.

Granja, Juan R. et al., "Studies on the Opening of Dioxanone and Acetal Templates and Applications to the Synthesis of 1α,25-Dihydroxyvitamin $D_2$," J. Org. Chem., 1993, vol. 58, pp. 124-131.

International Preliminary Report on Patentability and Written Opinion for PCT/US2007/008525 dated Oct. 8, 2008.

International Search Report and Written Opinion for PCT/US2007/008525 mailed Oct. 5, 2007.

Kiegiel, Jaroslaw et al., "Chemical Conversion of Vitamin $D_3$ to its 1.25-Dihydroxy Metabolite," Tetrahedron Letters, 1991, vol. 32, No. 43, pp. 6057-6060.

Konno, Katsuhiro et al., "A Novel and Practical Route to A-Ring Enyne Synthon for 1a,25-Dihydroxyvitamin $D_3$ Analogs: Synthesis of A-ring Diastereomers of 1a,25-Dihydroxy-Vitamin $D_3$ and 2-Methyl-1,25-Dihydroxyvitamin $D_3$," Bioorganic & Medicinal Chemistry Letters, 1998, vol. 8, pp. 151-156.

Lythgoe, B., "Synthetic Approaches to Vitamin D and its Relatives," Chem. Soc. Rev. 9, pp. 449-475.

Lythgoe, Basil et al., "Calciferol and its Relatives. Part 22. A Direct Total Synthesis of Vitamin $D_2$ and Vitamin $D_3$," J. Chem. Soc. Perkin Trans. I, 1978, pp. 590-595.

Mascarenas, J. L. et al., "Studies on the Synthesis of Side-Chain Hydroxylated Metabolites of Vitamind D. 3. Synthesis of 25-Ketovitamin $D_3$ and 25-Hydroxyvitamin $D_3$," J. Org. Chem., 1986, vol. 51, pp. 1269-1272.

Miyamoto, K., "Pharmaceuticals containing vitamin D3 derivatives for regulating calcium metabolism", Chemical Abstracts, Mar. 6, 1989, vol. 110: 82505v, No. 10, pp. 462-463.

Miyamoto, K., "2β-Substituted vitamin D derivatives", Chemical Abstracts, Nov. 21, 1994, vol. 121: 256121m, No. 21.

Okano, Toshio et al., "Regulatory Activities of 2β-(3-Hydroxypropoxy)-1a,25-Dihydroxyvitamin $D_3$, A Novel Synthetic Vitamin $D_3$ Derivative, on Calcium Metabolism," Biochemical and Biophysical Research Communications, Sep. 29, 1989, vol. 163, No. 3, pp. 1444-1449.

Ostrem, Voula K. et al., "24- and 26-homo-1,25-dihydroxyvitamin D3: Preferential activity in inducing differentiation of human leukemia cells HL-60 in vitro," Proc. Natl. Acad. Sci. USA, May 1987, vol. 84, pp. 2610-2614.

Ostrem, Voula K. et al., "Induction of Monocytic Differentiation of HL-60 Cells by 1,25-Dihydroxyvitamin D Analogs," The Journal of Biological Chemistry, Oct. 15, 1987, vol. 262, No. 29, pp. 14164-14171.

Perlman, Kato L. et al., "1α,25-Dihydroxy-19-Nor-Vitamin $D_3$, A Novel Vitamin D-related Compound with Potential Therapeutic Activity," Tetrahedron Letters, 1990, vol. 31, No. 13, pp. 1823-1824.

Perlman, Kato L. et al., "Novel Synthesis of 19-Nor-Vitamin D Compounds," Tetrahedron Letters, 1991, vol. 32, No. 52, pp. 7663-7666.

Plum, Lori A. et al., "Biologically active noncalcemic analogs of 1α,25-dihydroxyvitamin D with an abbreviated side chain containing no hydroxyl," PNAS, May 4, 2004, vol. 101, No. 81, pp. 6900-6904.

Posner, Gary H. et al., "2-Fluoroalkyl A-Ring Analogs of 1,25-Dihydroxyvitamin $D_3$ Stereocontrolled Total Synthesis via Intramolecular and Intermolecular Diels-Alder Cycloadditions. Preliminary Biological Testing," J. of Org. Chem., 1995, vol. 60, pp. 4617-4628.

Posner, Gary H. et al., "Stereocontrolled Synthesis of a Trihydroxylated a Ring as an Immediate Precursor to 1a,2a,25-Trihydroxovitamin $D_3$," J. Org. Chem., 1991, vol. 56, pp. 4339-4341.

Sarandeses, Luis A. et al., "Synthesis of 1a,25-Dihydroxy-19-Norprevitamin $D_3$," Tetrahedron Letters, 1992, vol. 33, No. 37, pp. 5445-5448.

Sardina, F. Javier et al., "Studies on the Synthesis of Side-Chain Hydroxylated Metabolites of Vitamin D. 2. Stereocontrolled Synthesis of 25-Hydroxyvitamin $D_2$," J. Org. Chem., 1986, vol. 51, pp. 1264-1269.

Sicinski, Rafal R. et al., "2-Ethyl and 2-Ethylidene Analogues of 1α,25-Dihydroxy-19-norvitamin $D_3$: Synthesis, Conformational Analysis, Biological Activities, and Docketing to the Modeled rVDR Ligand Binding Domain," J. Med Chem., 2002, vol. 45, pp. 3366-3380.

Sicinski, Rafal R. et al., "New 1α,25-Dihydroxy-19-Norvitamin $D_3$ Compounds of High Biological Activity: Synthesis and Biological Evaluation of 2-Hydroxymethyl, 2-Methyl, and 2-Methylene Analogues," J. Med Chem., 1998, vol. 41, pp. 4662-4674.

Sicinski, Rafal R. et al., "New highly calcemic 1α,25-dihydroxy-19-norvitamin $D_3$ compounds with modified side chain: 26,27-dihomo- and 26,27-dimethylene analogs in 20S-series," Steroids, 2002, vol. 67, pp. 247-256.

Slatopolsky, Eduardo et al., "A New Analog of Calcitriol, 19-Nor-1,25-$(OH)_2$ $D_2$ Suppresses Parathyroid Hormone Secretion in Uremic Rats in the Absence of Hypercalcemia," American Journal of Kidney Diseases, Nov. 1995, vol. 26, No. 5, pp. 852-860.

Suhara, Yoshitomo et al., "Synthesis and Biological Evaluation of Novel 2a-Substituted 1a,25-Dihydroxyvitamin $D_3$ Analogues," Bioorganic & Medicinal Chemistry Letters, 2000, vol. 10, pp. 1129-1132.

Toh, H. T. et al., "Studies on a Convergent Route to Side-Chain Analogues of Vitamin D: 25-Hydroxy-23-oxavitamin $D_3$," J. Org. Chem., 1983, vol. 48, pp. 1414-1417.

Non-Final Office Action for U.S. Appl. No. 12/437,892 dated Jun. 1, 2010.

1A-HYDROXY-2-(3'-HYDROXY-PROPYLIDENE)-19-NOR-VITAMIN D COMPOUNDS AND METHODS OF MAKING AND TREATMENT THEREOF

CROSS-REFERENCE TO RELATED APPLICATIONS

This application claims the benefit of U.S. Provisional Application Ser. No. 60/789,303 filed Apr. 5, 2006. The application is incorporated herein by reference in its entirety.

This application is related to U.S. Provisional Application Ser. Nos. 60/744,383; 60/744,385; 60/744,379; 60/744,381; 60/744,386; 60/791,487; and 60/791,227.

FIELD OF THE INVENTION

The instant invention relates to the field of Vitamin D analog compounds and methods of making and treatment thereof.

BACKGROUND OF THE INVENTION

The natural hormone, $1\alpha,25$-dihydroxyvitamin $D_3$ and its analog in the ergosterol series (i.e., $1\alpha,25$-dihydroxyvitamin $D_2$) are potent regulators of calcium homeostasis in animals and humans. Recently, its cellular differentiation activity has been established, see Ostrem et al., Proc. Natl. Acad. Sci. USA, 84, 2610 (1987). Structural analogs of these metabolites have been prepared and tested such as $1\alpha$-hydroxyvitamin $D_3$, $1\alpha$-hydroxyvitamin $D_2$, and, various side-chain homologated vitamins and fluorinated analogs thereof. Some of these compounds exhibit separation of activities in cell differentiation and calcium regulation. The difference in activity may be advantageous in treating a variety of diseases such as renal osteodystrophy, vitamin D-resistant rickets, osteoporosis, psoriasis, and other malignancies.

A class of vitamin D analogs, the 19-nor-vitamin D compounds, are characterized by replacement of the A-ring exocyclic methylene group at the carbon 19 (typical of the vitamin D system) with two hydrogen atoms. Biological testing of such 19-nor-analogs (e.g., $1\alpha,25$-dihydroxy-19-nor-vitamin $D_3$) revealed a selective activity profile having high potency to induce cellular differentiation and very low calcium mobilizing activity. Potentially, these compounds are useful therapeutic agents for treating renal osteodystrophy, vitamin D-resistant rickets, osteoporosis, psoriasis, other malignancies and various skin disorders.

Two different synthetic methods of making various 19-nor-vitamin D analogs have been described—See Perlman et al., Tetrahedron Letters 31, 1823 (1990); Perlman et al., Tetrahedron Letters 32, 7663 (1991); and, DeLuca et al., U.S. Pat. No. 5,086,191. Analogs of $1\alpha,25$-dihydroxy-19-norvitamin $D_3$ substituted at 2-position with hydroxy or alkoxy groups have also been synthesized (see DeLuca et al., U.S. Pat. No. 5,536,713) which may exhibit selective activity profiles.

Analogs characterized by the transposition of the A-ring exocyclic methylene group from carbon 10 (C10) to carbon 2 (C2) (e.g., 2-methylene-19-nor-vitamin D compounds) have been synthesized and tested. (See Sicinski et al., J. Med. Chem., 41, 4662 (1998); Sicinski et al., Steroids 67, 247 (2002); and, DeLuca et al., U.S. Pat. Nos. 5,843,928; 5,936,133 and 6,382,071). Molecular mechanics studies performed on these analogs predict that a change of A-ring conformation may cause flattening of the cyclohexanediol ring. Molecular mechanics calculations and NMR studies also predict that the A-ring conformational equilibrium would be ca. 6:4 in favor of the conformer having an equatorial $1\alpha$-OH. It was further predicted that introduction of the 2-methylene group into 19-nor-vitamin D carbon skeleton would change the character of its $1\alpha$- and $3\beta$-A-ring hydroxyls. They would both be in allylic positions similar to the $1\alpha$-hydroxyl group (which is important for biological activity) in the molecule of the natural hormone (i.e., $1\alpha,25$-$(OH)_2D_3$). It was found that $1\alpha,25$-dihydroxy-2-methylene-19-norvitamin D analogs are characterized by significant biological potency. In addition, the biological potency of such analogs may be enhanced dramatically where "unnatural" (20S) configuration is present.

Recently, 2-ethylidene analogs of $1\alpha,25$-dihydroxy-19-norvitamin $D_3$ have been synthesized whereby such modification of the A-ring resulted in significant biological potency particularly for the E-geometrical isomers, see Sicinski et al., J. Med. Chem., 45, 3366 (2002). It has been established that E-isomers have A-ring conformational equilibrium that is considerably shifted to the chair form possessing $1\alpha$-hydroxyl in equatorial orientation.

Recently, derivatives of $1\alpha,25$-dihydroxy-19-norvitamin $D_3$ having a 3'-hydroxypropylidene moiety at C-2 have been synthesized (see DeLuca et. al, U.S. Patent Application No. 2004/0229851) whereby the in vivo calcemic activity significantly exceeded that of $1\alpha,25$-$(OH)_2D_3$ particularly regarding stimulation of intestinal calcium transport. Molecular modeling studies of the analogs predicted that presence of an oxygen function (located at the terminus of the propylidene fragment) may promote interaction with the vitamin D receptor. The modeling further predicted that affinity of the synthesized compounds to VDR may approach that of the natural hormone. Taking into account the recent findings on 2-methylene-$1\alpha$-hydroxy-19-norvitamin D analogs having truncated side-chains, Plum et al., PNAS, 101, 6900 (2004), indicates that such compounds effectively suppress parathyroid hormone levels.

SUMMARY OF THE INVENTION

One aspect of the invention is a compound of Formula I comprising:

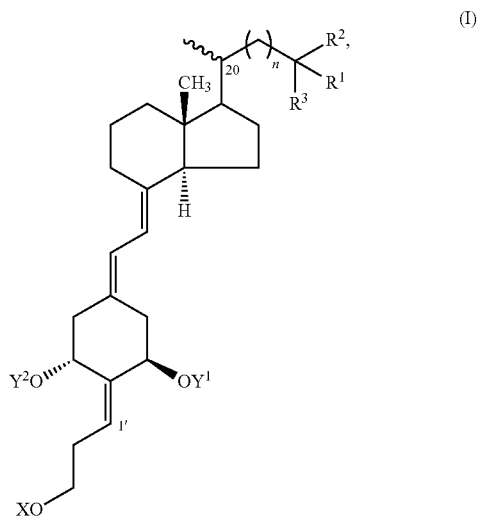

wherein the solid line to C1' provides that the compound is an E- or Z-geometrical isomer respecting the 2-propylidene segment, wherein the C20 is the stereochemical center, wherein the ~~~ provides an R or S configuration, wherein n is an integer from 1 to 3, wherein $Y^1$ is a member selected from the group consisting of hydrogen, deuterium and a first hydroxy-protecting group, wherein $Y^2$ is a member selected from the group consisting of hydrogen, deuterium and a second hydroxy-protecting group, wherein X is a third hydroxy-protecting group, wherein $R^1$ is a member selected from the group consisting of hydrogen, deuterium and methyl, wherein $R^2$ is a member selected from the group consisting of hydrogen, deuterium and methyl, wherein $R^3$ is a member selected from the group consisting of hydrogen, deuterium and methyl and wherein ⁓ is a member selected from the group consisting of ⋯⋯ and ▬,and esters of the compound thereof.

In another embodiment, X is a member selected from the group consisting of hydrogen, deuterium, $C_{1-10}$ branched or straight alkyl, $C_{1-10}$ branched or straight alkyl substituted with one or more hydroxy groups, $C_{1-10}$ branched or straight alkyl substituted with one or more $C_{1-10}$ branched or straight alkoxy groups, $C_{1-10}$ branched or straight alkyl substituted with one or more aryloxy groups, carbonyl substituted with one or more $C_{1-10}$ branched or straight alkoxy group, $C_{1-6}$ branched or straight alkanoyl, $C_{1-6}$ branched or straight carboxyalkanoyl, aromatic acyl, silyl substituted with one or more $C_{1-10}$ branched or straight alkyl groups, silyl substituted with one or more $C_{1-10}$ branched or straight alkyl groups and silyl substituted with one or more aryl groups.

In another embodiment, the carbonyl substituted with a $C_{1-10}$ branched or straight alkoxy group is a member selected from the group consisting of methoxycarbonyl, ethoxycarbonyl, propoxycarbonyl, iso-propoxycarbonyl, butoxycarbonyl, isobutoxycarbonyl, tert-butoxycarbonyl, benzyloxycarbonyl and allyloxycarbonyl.

In another embodiment, the $C_{1-6}$ branched or straight carboxyalkanoyl is a member selected from the group consisting of oxalyl, malonyl, succinyl and glutaryl.

In another embodiment, the aromatic acyl is a member selected from the group consisting of benzoyl, halo-substituted benzoyl, nitro-substituted benzoyl and $C_{1-10}$ straight or branched alkyl-substituted benzoyl.

In another embodiment, the $C_{1-10}$ branched or straight alkyl substituted with one or more $C_{1-10}$ branched or straight alkoxy groups is a member selected from the group consisting of methoxymethyl, ethoxymethyl, methoxyethoxymethyl, tetrahydrofuranyl and tetrahydropyranyl.

In another embodiment, the silyl substituted with one or more $C_{1-10}$ branched or straight alkyl groups is a member selected from the group consisting of trimethylsilyl, triethylsilyl, t-butyldimethylsilyl and dibutylmethylsilyl.

In another embodiment, the silyl substituted with one or more aryl groups is a member selected from the group consisting of diphenylmethylsilyl, phenyldimethylsilyl and diphenyl-t-butylsilyl.

In another embodiment, the $C_{1-10}$ branched or straight alkyl substituted with one or more aryloxy groups is a member selected from the group consisting of phenyl-substituted phenyl, $C_{1-10}$ straight or branched alkyl-substituted phenyl, nitro-substituted phenyl and halo-substituted phenyl.

In another embodiment, the compound is an E-geometrical isomer. Alternatively, the compound is a Z-geometrical isomer.

In another embodiment, X is t-butyldimethylsilyl. $Y^1$ may be t-butyldimethylsilyl. $Y^2$ may be t-butyldimethylsilyl. Alternatively, X is hydrogen. $Y^1$ may be hydrogen. $Y^2$ may be hydrogen.

In another embodiment, n is 1, $R^1$ and $R^2$ are methyl, and $R^3$ is hydrogen.

In another embodiment, the compound is an E-isomer of (20R)-1α-hydroxy-2-(3'-hydroxypropylidene)-19,24,25,26,27-penta-nor-vitamin $D_3$.

In another embodiment, the compound is an E-isomer of (20S)-1α-hydroxy-2-(3'-hydroxypropylidene)-19,24,25,26,27-penta-nor-vitamin $D_3$.

In another embodiment, the compound is an E-isomer of (20R)-1α-hydroxy-2-(3'-hydroxypropylidene)-19,23,24-tri-nor-vitamin $D_3$.

In another embodiment, the compound is an E-isomer of (20S)-1α-hydroxy-2-(3'-hydroxypropylidene)-19,23,24-tri-nor-vitamin $D_3$.

Another aspect of the invention includes a method of making a hydrindanone intermediate compound for use in making the compound of Formula I, wherein n is 1, wherein $R^1$, $R^2$, and $R^3$ are each hydrogen and wherein ⁓ is ⋯⋯, comprising the steps of:

providing a starting compound of the Formula II:

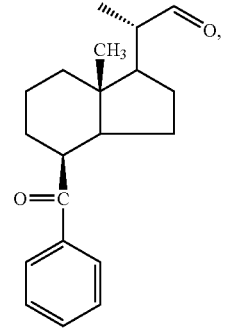

(II)

reacting the starting compound with a ylide reactant to produce an alkene-containing product, hydrogenating the alkene-containing product to produce an oily ester product, hydrolysing the oily ester product to produce an alcohol product and oxidizing the alcohol product to produce the hydrindanone intermediate compound having the Formula III:

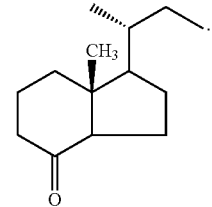

(III)

Another aspect of the invention includes a method of making the compound of Formula I, wherein n is 1, wherein $R^1$, $R^2$, and $R^3$ are each hydrogen and wherein ⁓ is ⋯⋯, comprising: coupling the hydrindanone intermediate compound of Formula III with lithium phosphinoxy carbanion to produce a coupled product having the protecting groups and hydrolyzing the protecting groups.

Another aspect of the invention includes a method of making a hydrindanone intermediate compound for use in making the compound Formula I, wherein n is 1, wherein $R^1$, $R^2$, and $R^3$ are each hydrogen and wherein ⁓ is ▬, comprising the steps of: providing a starting compound of the Formula IV:

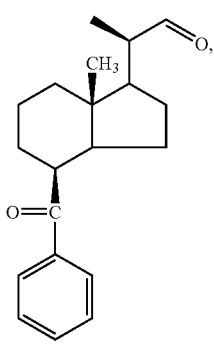

(IV)

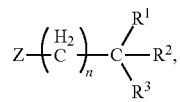

(VII)

wherein n is an integer from 1 to 3, wherein Z is a member selected from the group consisting of Br, Cl and I and wherein at least one of $R^1$, $R^2$ or $R^3$ is a methyl to produce an alkylated nitrile product, hydrolysing the alkylated nitrile product to produce a hydroxy nitrile product, reductively decyanating the hydroxy nitrile product to produce a mixture of epimeric alcohol products, oxidizing the mixture of epimeric alcohol products to produce a mixture of a 20S-ketone product and a 20R-ketone product, separating the 20S-ketone and 20R-ketone products, coupling the 20R-ketone product with lithium phosphinoxy carbanion to produce a coupled 20R product having the protecting groups and hydrolysing the protecting groups. In another embodiment of the method, n is 1, Z is Br, $R^1$ and $R^2$ are methyl and $R^3$ is hydrogen.

reacting the starting compound with a ylide reactant to produce an alkene-containing product, hydrogenating the alkene-containing product to produce an oily ester product, hydrolysing the oily ester product to produce an alcohol product and oxidizing the alcohol product to produce the hydrindanone intermediate compound having the Formula V:

Another aspect of the invention is a method of making the compound of Formula
I, wherein at least one of $R^1$, $R^2$ or $R^3$ is a methyl and wherein ∿∿ is ▬▬,, comprising the steps of: providing a starting compound of the Formula VIII:

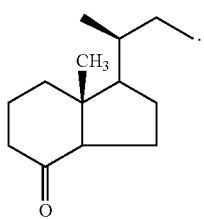

(V)

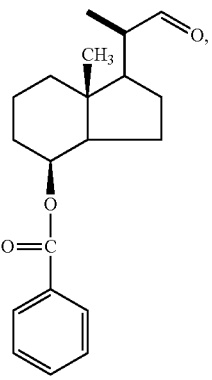

(VIII)

Another aspect of the invention includes a method of making the compound of Formula I, wherein n is 1, wherein $R^1$, $R^2$, and $R^3$ are each hydrogen and wherein ∿∿ is ▬▬,comprising the steps of: coupling the hydrindanone intermediate compound of Formula V with lithium phosphinoxy carbanion to produce a coupled product having the protecting groups and hydrolyzing the protecting groups.

Another aspect of the invention includes a method of making the compound of Formula I, wherein at least one of $R^1$, $R^2$ or $R^3$ is a methyl and wherein ∿∿ is ⦀⦀,, comprising the steps of: providing a starting compound of the Formula VI:

wherein ▬▬ is a member selected from the group consisting of ⦀⦀ and ▬▬,, converting the starting compound into a nitrile compound, alkylating the nitrile compound with a first reactant of the Formula VII:

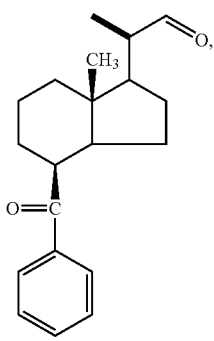

(VI)

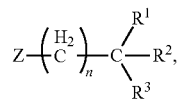

(VII)

wherein n is an integer from 1 to 3, wherein Z is a member selected from the group consisting of Br, Cl and I and wherein at least one of $R^1$, $R^2$ or $R^3$ is a methyl, to produce an alkylated nitrile product, hydrolysing the alkylated nitrile product to produce a hydroxy nitrile product, reductively decyanating the hydroxy nitrile product to produce a mixture of epimeric alcohol products, oxidizing the mixture of epimeric alcohol products to produce a mixture of a 20S-ketone product and a 20R-ketone product, separating the 20S-ketone and 20R-ketone products, coupling the 20S-ketone product with lithium wherein ▬▬ is a member selected from the group consisting of ⦀⦀ and ▬▬,, converting the starting compound into a nitrile compound, alkylating the nitrile compound with a first reactant of the Formula VII:

phosphinoxy carbanion to produce a coupled 20S product having the protecting groups and hydrolysing the protecting groups. In another embodiment of the method, n is 1, Z is Br, $R^1$ and $R^2$ are methyl and $R^3$ is hydrogen.

BRIEF DESCRIPTION OF THE EXEMPLARY DRAWINGS

FIG. 1 is a graph illustrating the relative activity of (20S)-1α-hydroxy-2-(3'-hydroxypropylidene)-19,23,24-tri-nor-vitamin $D_3$ ("HPBS") and (20R)-1α-hydroxy-2-(3'-hydroxypropylidene)-19,23,24-tri-nor-vitamin $D_3$ ("HPBR") as against 1α,25-dihydroxyvitamin $D_3$ in terms of competitive VDR binding (i.e., binding to the 1α,25-dihydroxyvitamin $D_3$ pig intestinal nuclear receptor), whereby the procedure set forth in Dame et al (Biochemistry 25, 4523-4534 (1986)) was followed.

FIG. 2 is a graph illustrating the relative activity of (20R)-1α-hydroxy-2-(3'-hydroxypropylidene)-19,24,25,26,27-penta-nor-vitamin $D_3$ ("RBH") and (20S)-1α-hydroxy-2-(3'-hydroxypropylidene)-19,23,24-tri-nor-vitamin $D_3$ ("SBH") as against 1α,25-dihydroxyvitamin $D_3$ in terms of competitive VDR binding (i.e., binding to the 1α,25-dihydroxyvitamin $D_3$ pig intestinal nuclear receptor), whereby the procedure set forth in Dame et al (Biochemistry 25, 4523-4534 (1986)) was followed.

FIG. 3 is a graph illustrating the percent HL-60 cell differentiation activity of 1α,25-dihydroxyvitamin $D_3$, RBH, and SBH as a function of concentration in the medium, whereby the differentiation of HL-60 promyelocytic into monocytes was determined as set forth in Ostrem et al (J. Biol. Chem. 262, 14164-14171 (1987)).

FIG. 4 is a graph illustrating the percent HL-60 cell differentiation activity of 1α,25-dihydroxyvitamin $D_3$, HPBS, and HPBR as a function of concentration in the medium, whereby the differentiation of HL-60 promyelocytic into monocytes was determined as set forth in Ostrem et al (J. Biol. Chem. 262, 14164-14171 (1987)).

FIG. 5 is a graph illustrating the transcriptional activity of 1α,25-dihydroxyvitamin $D_3$, RBH, and SBH as a function of concentration, whereby transcriptional activity was measured in ROS 17/2.8 (bone) cells that were stably transfected with a 24-hydroxylase ("24OHase") gene promoter upstream of a luciferase reporter gene (see Arbour et al, (1998); and Arbour et al, Nat. Genet. 25; 187 (2000)), whereby cells were given a range of doses, whereby cells were harvested 16 hours after dosing, and the luciferase activities were measured using a luminometer, and whereby "RLU" refers to relative luciferase units.

FIG. 6 is a graph illustrating the transcriptional activity of 1α,25-dihydroxyvitamin $D_3$, HPBR, and HPBS as a function of concentration, whereby transcriptional activity was measured in ROS 17/2.8 (bone) cells that were stably transfected with a 24-hydroxylase ("24OHase") gene promoter upstream of a luciferase reporter gene (see Arbour et al, (1998); and Arbour et al (2000)), whereby cells were given a range of doses, whereby cells were harvested 16 hours after dosing, and the luciferase activities were measured using a luminometer, and whereby "RLU" refers to relative luciferase units.

DETAILED DESCRIPTION OF PREFERRED EMBODIMENTS

Figure 1:
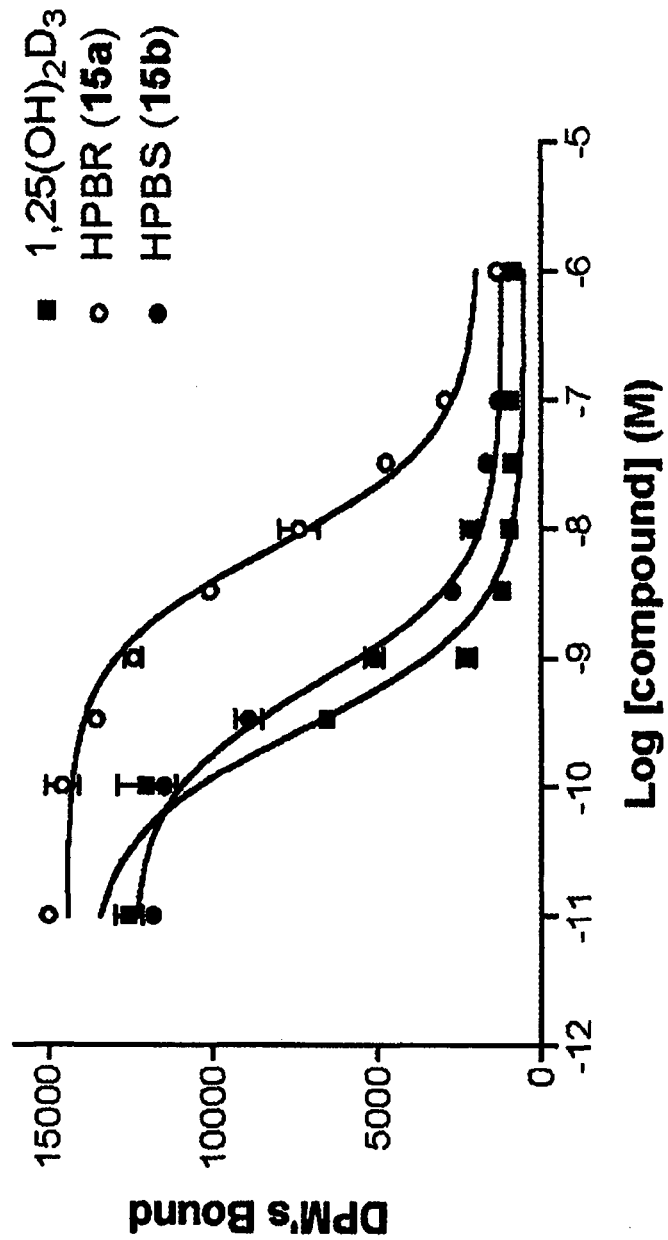
Figure 2:
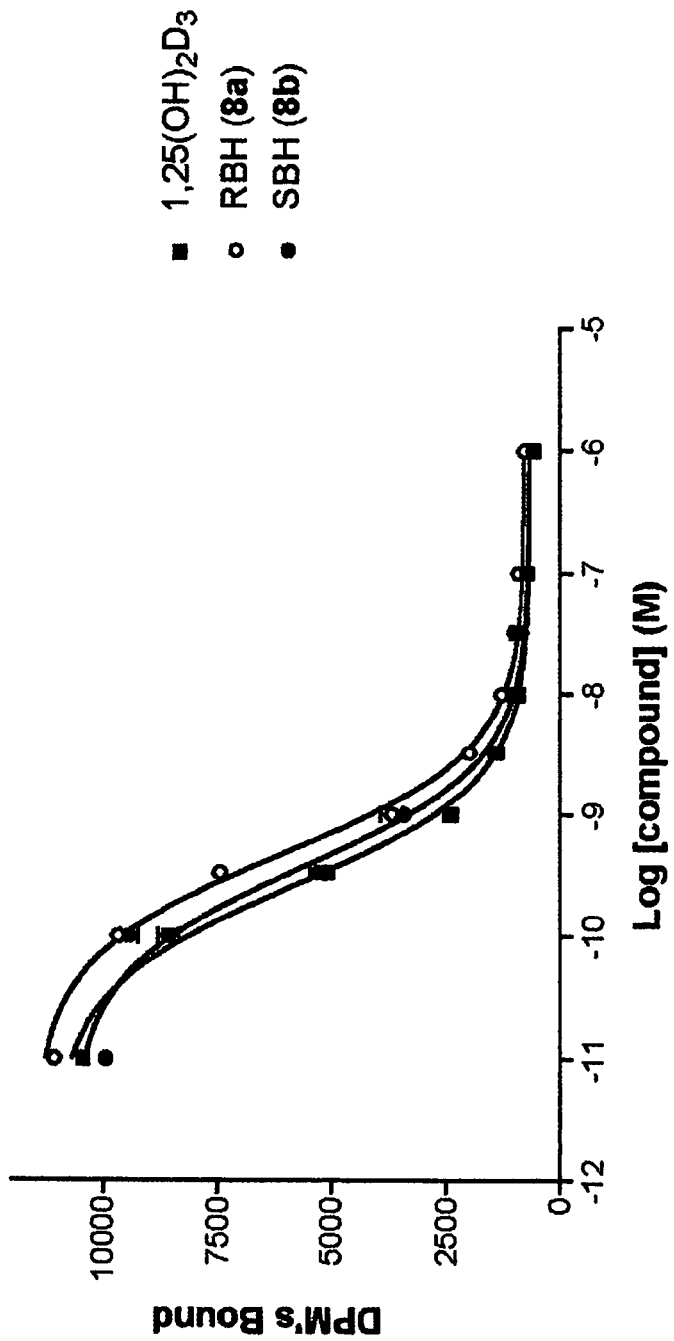
Figure 3:
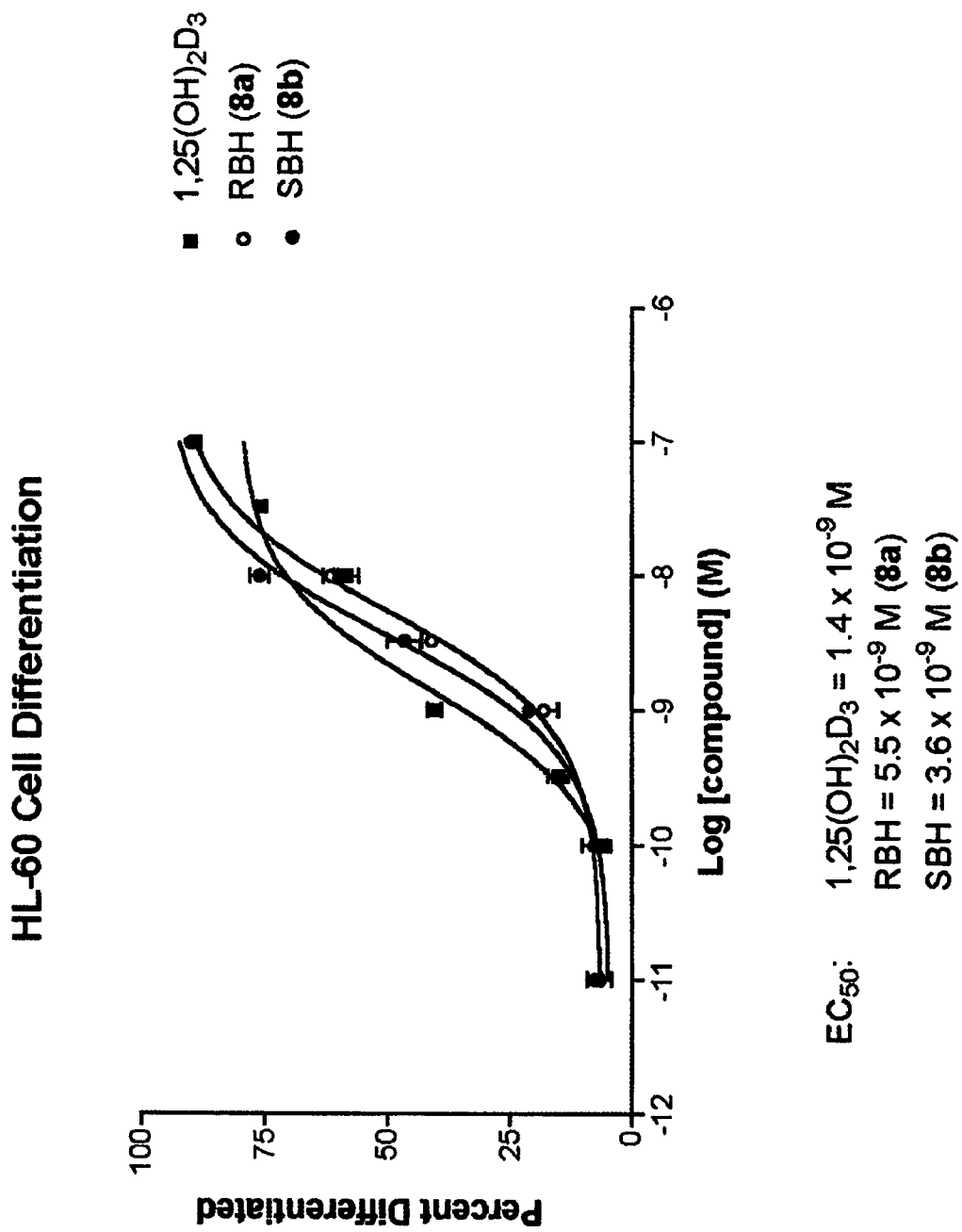
Figure 4:
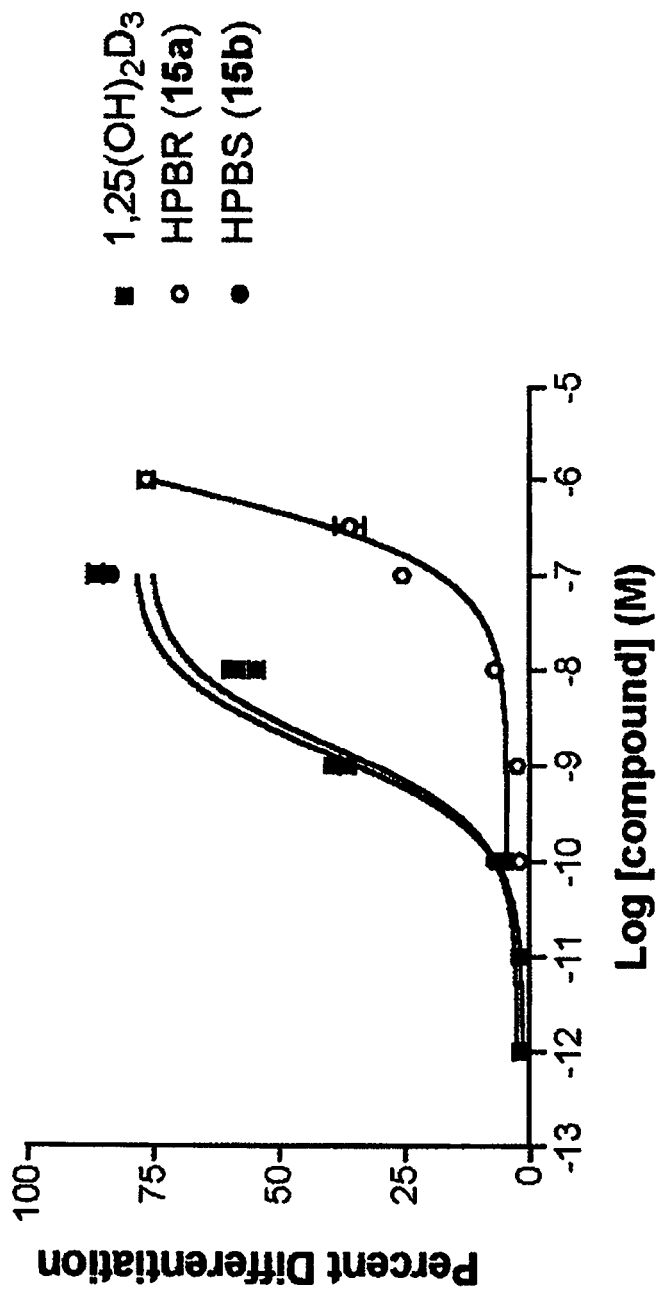
Figure 5:
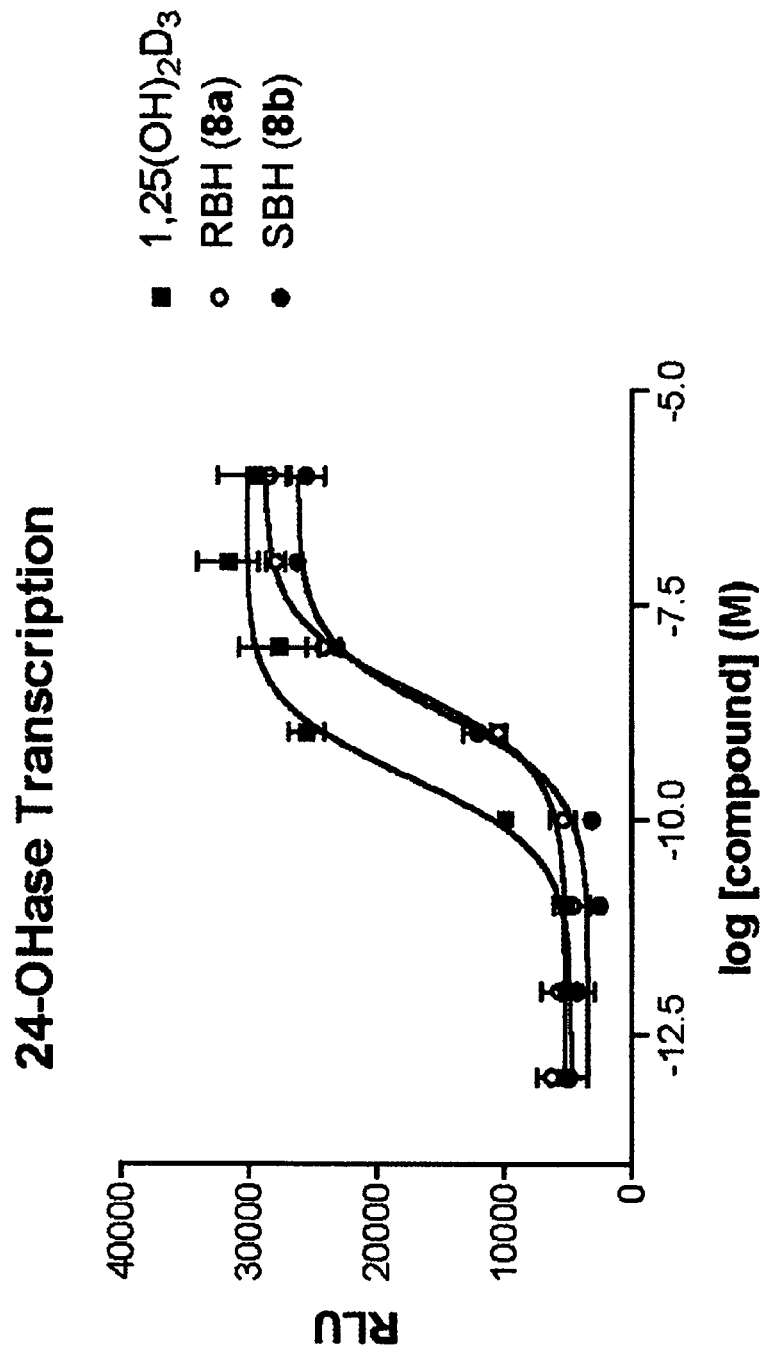
Figure 6:
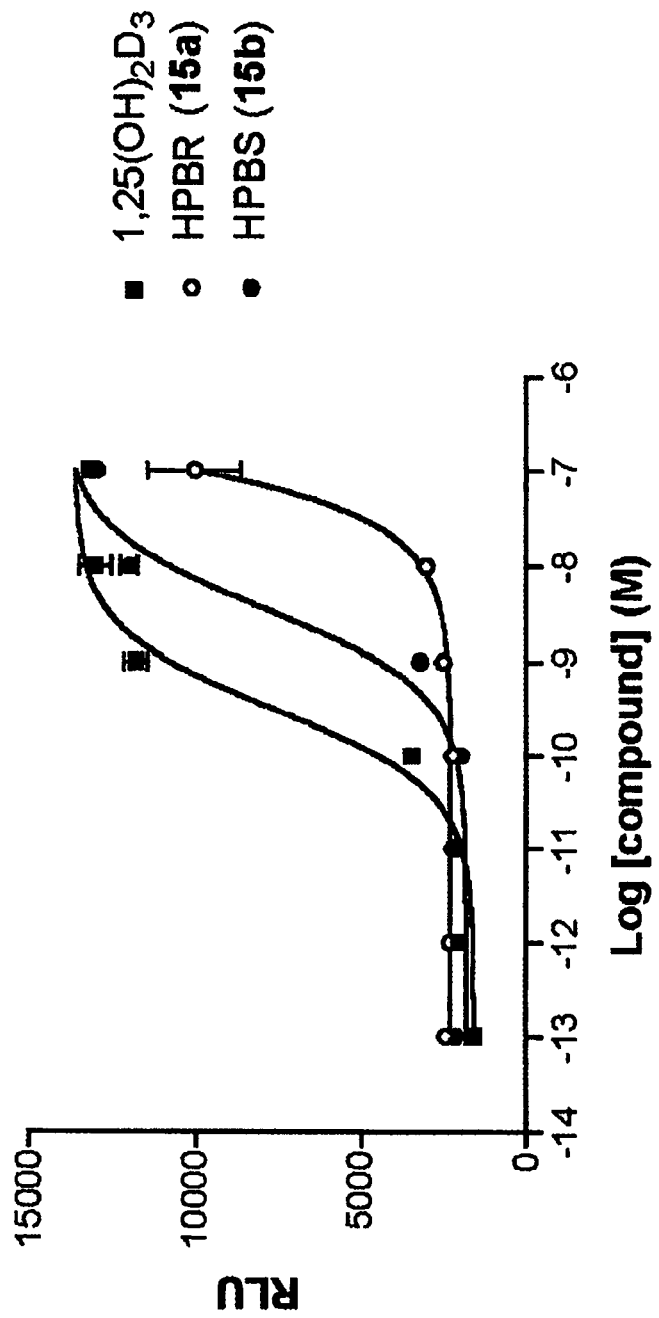
Figure 7:
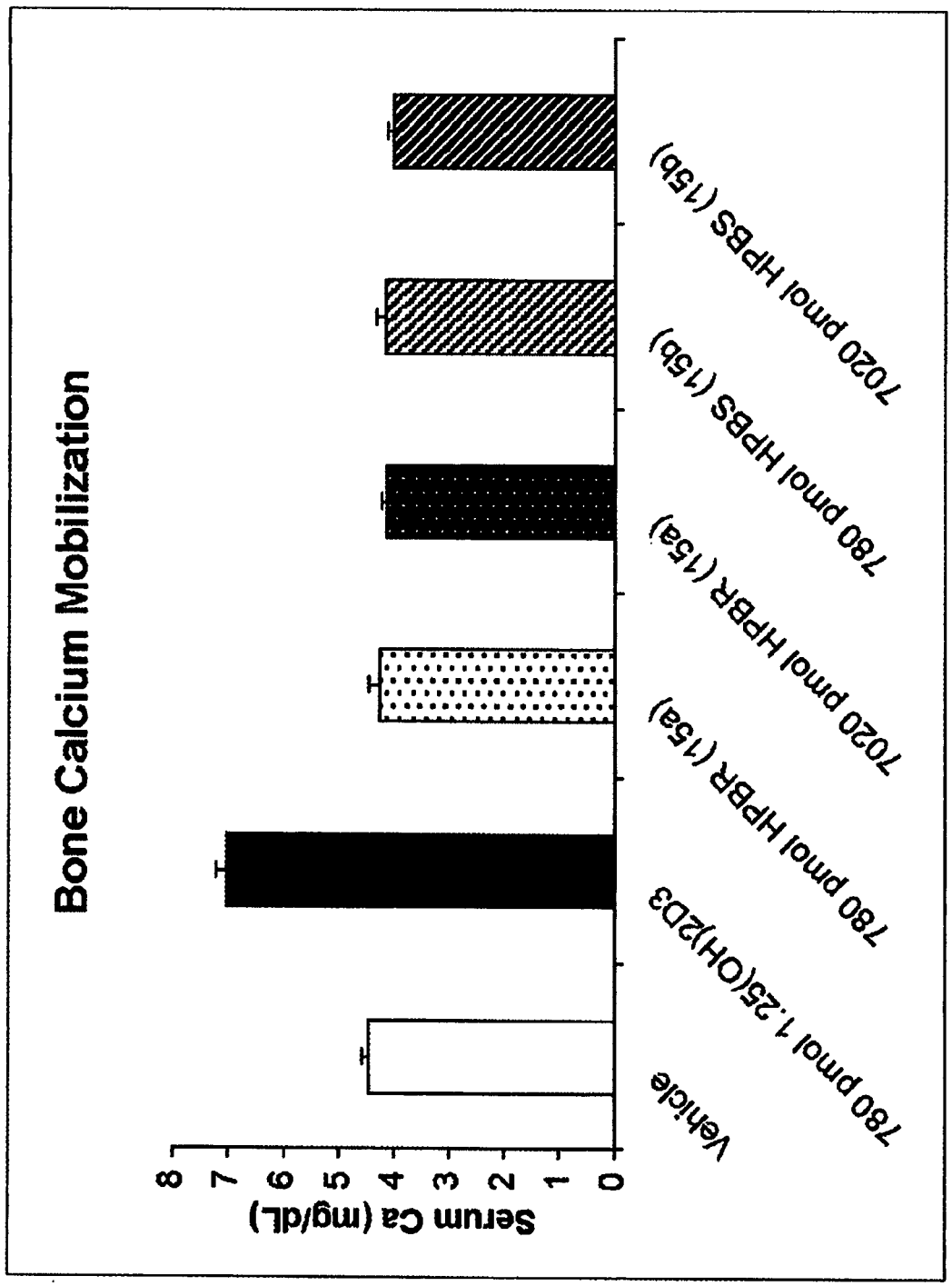
FIG. 7 is bar graphs illustrating bone calcium mobilization activity of 1α,25-dihydroxyvitamin $D_3$, HPBR, and HPBS administered at various doses to vitamin D deficient rats on a low calcium diet, whereby the rise in serum calcium concentration reflects the mobilization of bone calcium.
Figure 8:
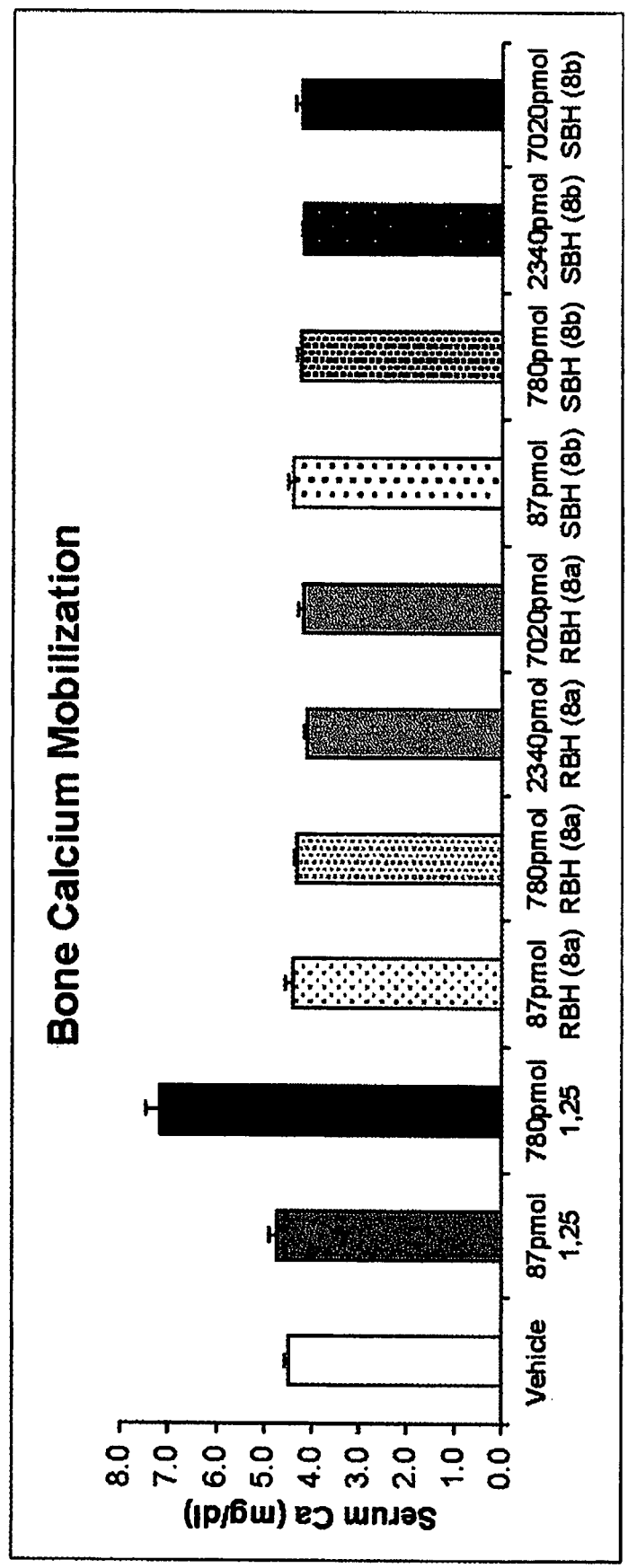
FIG. 8 is a bar graph illustrating bone calcium mobilization activity of the vehicle (i.e., control), 1α,25-dihydroxyvitamin $D_3$, RBH and SBH administered at various doses to vitamin D deficient rats on a low calcium diet, whereby the rise in serum calcium concentration reflects the mobilization of bone calcium.
Figure 9:
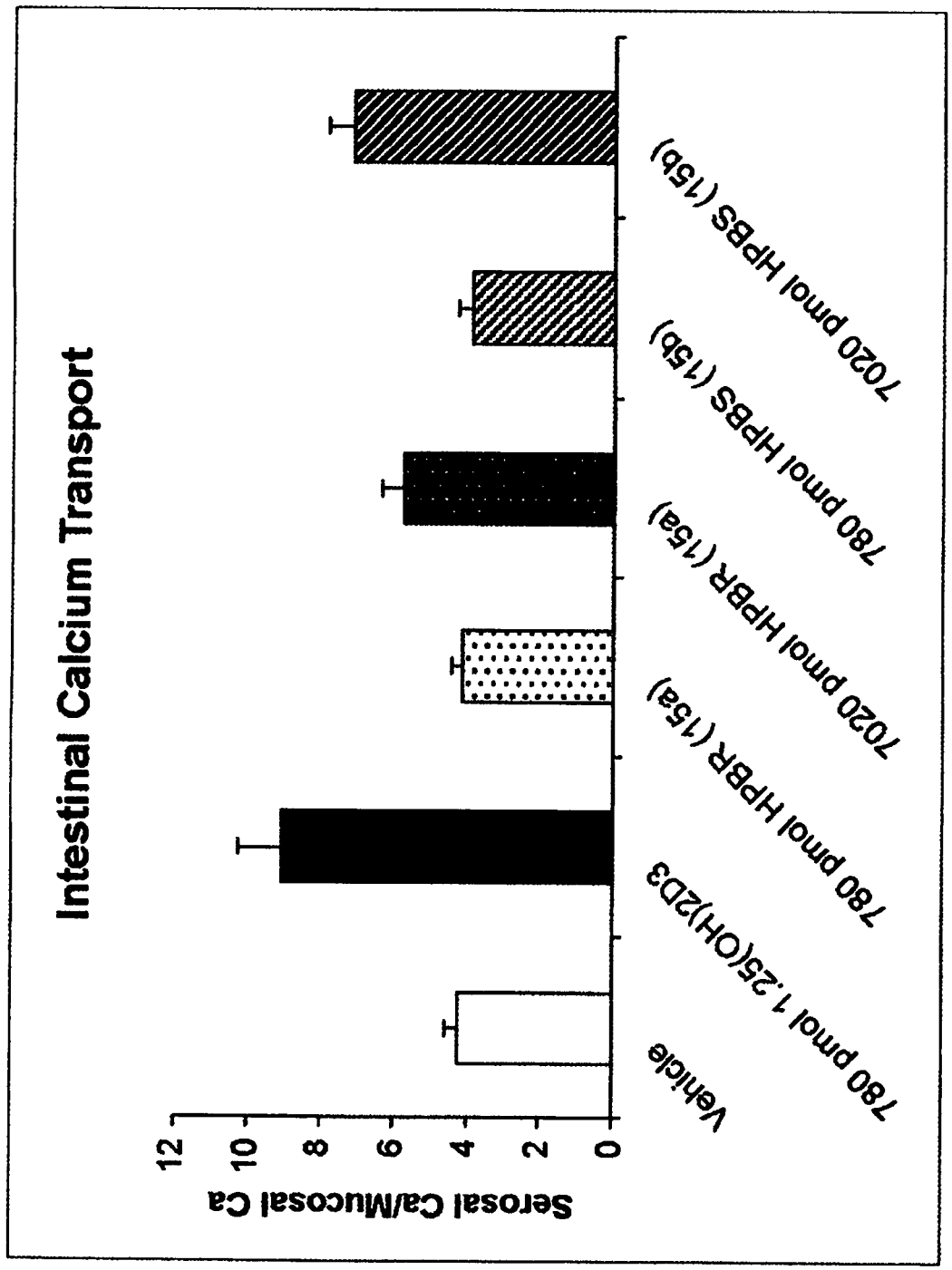
FIG. 9 is a bar graph illustrating intestinal calcium transport activity of the vehicle, 1α,25-dihydroxyvitamin $D_3$, HPBR, and HPBS administered at various doses to vitamin D deficient rats on a low calcium diet, whereby the intestinal calcium transport was measured by the everted intestinal gut sac method.
Figure 10:
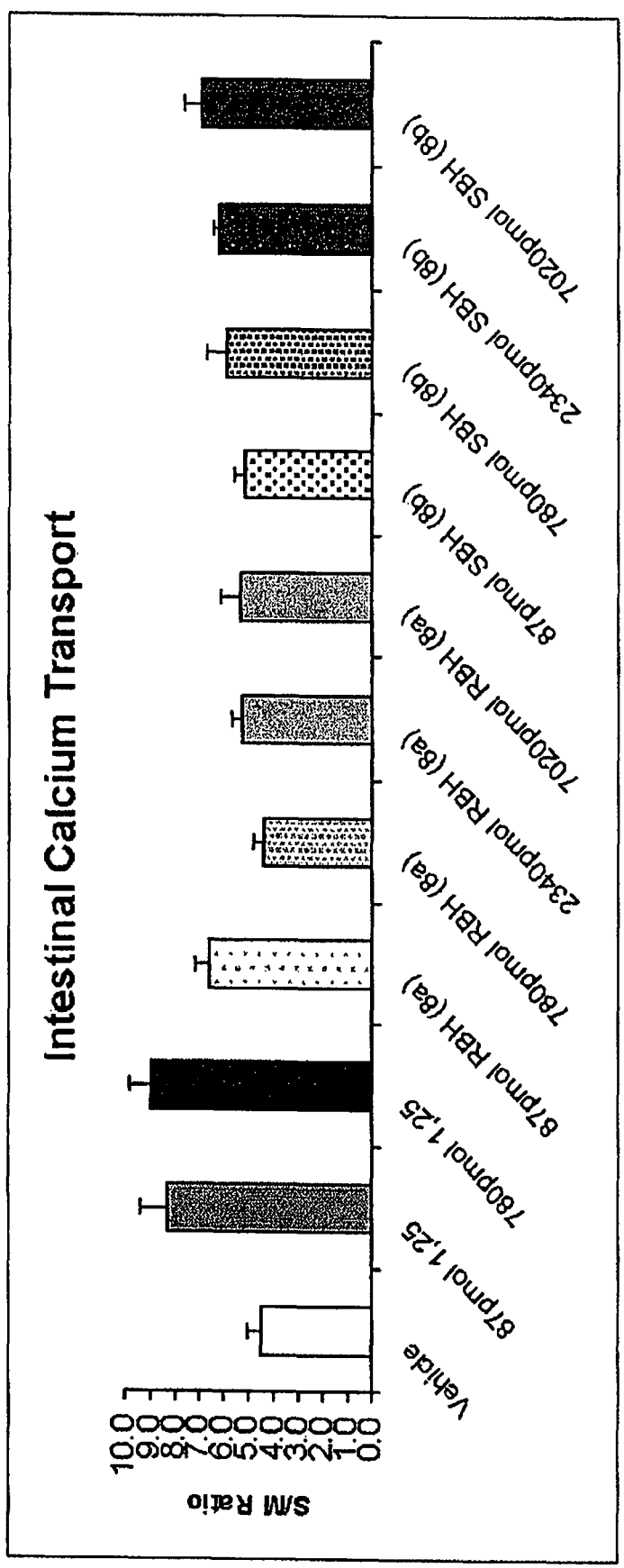
FIG. 10 is a bar graph illustrating intestinal calcium transport activity of the vehicle, 1α,25-dihydroxyvitamin $D_3$, RBH, and SBH administered at various doses to vitamin D deficient rats on a low calcium diet, whereby the intestinal calcium transport was measured by the everted intestinal gut sac method.

The instant invention is generally directed to biologically active 2-alkylidene-19-norvitamin D compounds and analogs thereof characterized by the presence of a 3'-hydroxypropylidene moiety at C2 and the presence of an abbreviated alkyl side-chain free of any hydroxyl moiety.

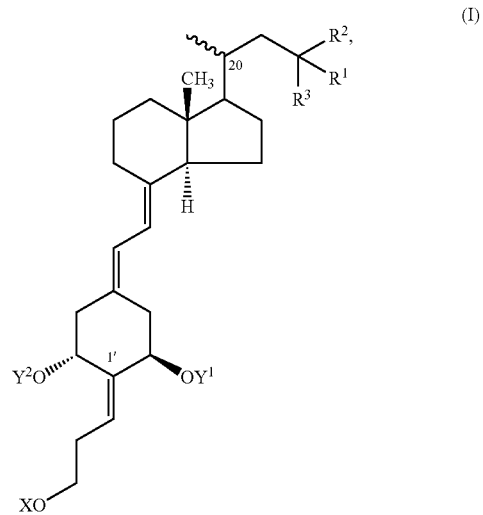

wherein $Y_1$ and $Y_2$ (which may be the same or different) is selected from the group consisting of hydrogen and a hydroxy-protecting group; wherein X is a member selected from the group consisting of alkyl, hydrogen, hydroxy-protecting group, hydroxyalkyl, alkoxyalkyl and aryloxyalkyl; and, wherein $R_1$, $R_2$ and $R_3$ (which may be the same or different) are selected from the group consisting of hydrogen or methyl. The wavy line attached to C20 indicates that the compound is in either the R or S configuration. The relative position of the 2-propylidene unit at the C1' indicates the E,Z geometrical isomer configuration relative to the remainder of the molecule.

Exemplary side-chains having a natural 20R- and "unnatural" 20S-configuration includes the structures represented by formulas (a), (b), (c) and (d) below. That is, the side-chain in 24,25,26,27-tetranorvitamin $D_3$ (also referred to as "bishomopregnacalciferol" and RBH herein); 20S-24,25,26,27-tetranorvitamin $D_3$ (also referred to as "20S-bishomopregnacalciferol" and SBH herein)(b); 23,24-dinorvitamin $D_3$ (also referred to as HPBR herein)(c); and, 20S-23,24-dinorvitamin D$_3$ (also referred to as HPBS herein)(d).

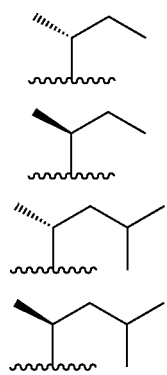

Preparation of 1α-hydroxy-19-nor-vitamin D compounds having the substituted propylidene moiety at C2, of the basic structure I can be accomplished by the condensation of a bicyclic Windaus-Grundmann type ketone II with the allylic phosphine oxide III as set forth below.

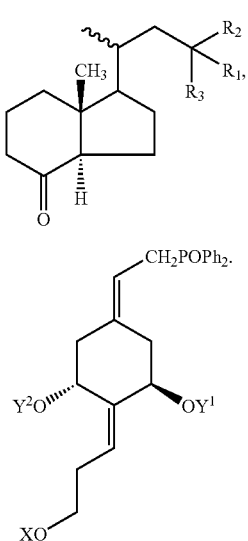

Regarding Formulas II and III, groups $Y_1$, $Y_2$, X, $R_1$, $R_2$ and $R_3$ represent groups defined hereinabove; and, preferably, $Y_1$, $Y_2$, X are hydroxy-protecting groups. The process is an application of the convergent synthesis concept which has been used to prepare vitamin D compounds. (See, e.g., Lythgoe et al., J. Chem. Soc. Perkin Trans. I, 590 (1978); Lythgoe, Chem. Soc. Rev. 9, 449 (1983); Toh et al., J. Org. Chem. 48, 1414 (1983); Baggiolini et al., J. Org. Chem. 51, 3098 (1986); Sardina et al., J. Org. Chem. 51, 1264 (1986); J. Org. Chem. 51, 1269 (1986); DeLuca et al., U.S. Pat. No. 5,086,191; and, DeLuca et al., U.S. Pat. No. 5,536,713).

The phosphine oxides of III are available or can be prepared from commercially available (1R,3R,4S,5R)-(−)-quinic acid. (See Glebocka et al., J. Steroid Biochem. Mol. Biol. 89-90, 25 (2004); and, DeLuca et. al, US Patent Application No. 2004/0229851).

Regarding preparation of the hydrindanones of II, alternative synthetic routes start from the epimeric at C20 and the 22-aldehydes of 1a and 1b. (See Fall et al., Tetrahedron Lett. 43, 1433 (2002); Granja et al., J. Org. Chem. 58, 124 (1993)). As set forth in SCHEME I, separate analogous processes transform starting aldehydes 1a and 1b into C,D-ring synthons 5a,b that are subsequently coupled with phosphine oxide 6. Aldehydes 1a and 1b were reacted with a ylide generated from methyltriphenylphosphonium bromide and n-butyllithium (i.e., a Wittig reaction). The resulting olefins 2a and 2b were hydrogenated generating saturated compounds 3a and 3b possessing side chains having 4 carbons. Basic hydrolysis of the ester group produced the 8β-alcohols 4a and 4b that were subsequently oxidized with tetrapropylammonium perruthenate to make the hydrindanones 5a and 5b. Wittig-Horner coupling of the Grundmann ketones 5a and 5b with lithium phosphinoxy carbanion, generated from the phosphine oxide (6) (prepared in accordance with DeLuca et. al, U.S. Patent Application No. 2004/0229851, which is incorporated herein by reference) provided the protected vitamin compounds 7a and 7b. After deprotecting with tetrabutylammonium fluoride, 1α-hydroxy-2-[3α-hydroxypropylidene]-19,24,25,26,27-pentanorvitamin D$_3$ compounds 8a and 8b were made. 1α-hydroxy-2-[3'-hydroxypropylidene]-19,24,25,26,27-pentanorvitamin D$_3$ (8a) is described in EXAMPLE I herein and preparation of its 20S-epimer 8b is in EXAMPLE II herein.

SCHEME II shows preparation of the vitamin D analogs having iso-branched alkyl substituents (i.e., iso-butyl) attached to C20 and starting from the same 22-aldehyde 1a. Aldehyde 1a was transformed into a mixture of isomeric E- and Z-oximes which (upon heating with acetic anhydride) formed the nitrile 9. The nitrile 9 was treated with LDA producing carbanion alkylated by addition of iso-butyl bromide. X-Ray analysis showed that the single alkylation product (10) possessed 20S-configuration.

Subsequently, alkaline hydrolysis of 8β-benzoyloxy group in the nitrile 10 produced the corresponding alcohol 11 which is desirable for reductive removal of the C20 cyano group, whereby the conditions required for such decyanation process could otherwise cause the reduction of the 8-benzoyloxy group to the corresponding alkane (8-unsubstituted derivative). 8β-Hydroxy group in alcohol 11 could be protected as alkylsilyl-, arylsilyl or alkoxyalkyl ether before the decyanation process. Several methods for the reductive decyanation of alcohol 11 are available, whereby dissolving metal reductions are preferred.

For example, alcohol 11 can be transformed into a mixture of alcohols 12a and 12b by reacting with potassium metal in hexamethylphosphoric triamide and tert-butanol or by reacting with a potassium metal/dicyclohexano-18-crown-6/toluene system. 8β-Alcohols 12a and 12b were subsequently oxidized with tetrapropylammonium perruthenate to make the hydrindanones 13a and 13b. Separation of the Grundmann ketones (epimeric at C20) was achieved using HPLC. Wittig-Horner coupling of the hydrindanones 13a and 13b was performed using lithium phosphinoxy carbanion generated from the phosphine oxide 6 and phenyllithium producing protected vitamin compounds 14a and 14b. After de-protecting with tetrabutylammonium fluoride, 1α-hydroxy-2-[3'-hydroxypropylidene]-19,23,24-trinorvitamin D$_3$ compounds (15a,b) was produced.

As set forth in EXAMPLE III, synthesis of 1α-hydroxy-2-[3'-hydroxypropylidene]-19,23,24-trinorvitamin D$_3$ (15a) and its epimer 15b is shown. It is appreciated that other 1α-hydroxy-2-[3'-hydroxypropylidene]-19-nor-vitamin D analogs having the instant alkyl side-chains may be synthesized by the methods set forth herein.

This invention is described by the following illustrative examples. In these examples specific products identified by Arabic numerals (e.g. 1, 2, 3, etc) refer to the specific structures identified in the preceding description and in the SCHEME I and SCHEME II.

EXAMPLES

Chemistry. Melting points (uncorrected) were determined using a Thomas-Hoover capillary melting-point apparatus. Ultraviolet (UV) absorption spectra were recorded using a Perkin-Elmer Lambda 3B UV-VIS spectrophotometer in ethanol. $^1$H nuclear magnetic resonance (NMR) spectra were recorded at 400 MHz using a Bruker Instruments DMX-400 Avance console spectrometer in deteriochloroform. Chemical shifts (δ) were determined downfield from internal Me$_4$Si (δ 0.00). Electron impact (EI) mass spectra were determined using a Micromass AutoSpec (Beverly, Mass.) instrument. High-performance liquid chromatography (HPLC) was determined using a Waters Associates liquid chromatograph equipped with a Model 6000A solvent delivery system, a Model U6K Universal injector and a Model 486 tunable absorbance detector. THF was freshly distilled before use from sodium benzophenone ketyl under argon.

Biological Activity; Vitamin D Receptor Binding; Test Material and Protein Source. Full-length recombinant rat receptor was expressed in *E. coli* BL21(DE3) Codon Plus RIL cells and purified to homogeneity using two different column chromatography systems. The first system was a nickel affinity resin that utilized the C-terminal histidine tag on the protein. The protein eluted from the resin was further purified using ion exchange chromatography (S-Sepharose Fast Flow). Aliquots of the purified protein were quick frozen in liquid nitrogen and stored at −80° C. until use. For use in binding assays, the protein was diluted in TEDK$_{50}$ (50 mM Tris, 1.5 mM EDTA, pH=7.4, 5 mM DTT, 150 mM KCl) with 0.1% Chaps detergent. The receptor protein and ligand concentration was optimized such that no more than 20% of the added radiolabeled ligand was bound to the receptor.

Unlabeled ligands were dissolved in ethanol, and the concentrations were determined using UV spectrophotometry (1.25(OH)$_2$D$_3$: molar extinction coefficient=18,200 and λ$_{max}$=265 nm; Analogs: molar extinction coefficient=42,000 and λ$_{max}$=252 nm). Radiolabeled ligand ($^3$H-1.25(OH)$_2$D$_3$) was added in ethanol at a final concentration of 1 nM.

Radiolabeled and unlabeled ligands were added to 100 mcl of the diluted protein at a final ethanol concentration of <10%, mixed and incubated overnight on ice to reach binding equilibrium. The following day, 100 mcl of hydroxylapatite slurry (50%) was added to each tube and mixed at 10-minute intervals for 30 minutes. The hydroxylapatite was collected by centrifugation and then washed 3 times with Tris-EDTA buffer (50 mM Tris, 1.5 mM EDTA, pH 7.4) containing 0.5% Titron X-100. After the final wash, the pellets were transferred to scintillation vials containing 4 ml of Biosafe II scintillation cocktail, mixed and placed in a scintillation counter. Total binding was determined from the tubes containing only radiolabeled ligand.

HL-60 Differentiation and Test Material. The drugs were dissolved in ethanol, and the concentration was determined using UV spectrophotometry. Serial dilutions were prepared so that a range of drug concentrations could be tested without changing the final concentration of ethanol (≦0.2%) present in the cell cultures. Human promyelocytic leukemia ("HL-60") cells were grown in RPMI-1640 medium containing 10% fetal bovine serum. The cells were incubated at 37° C. in the presence of 5% CO$_2$. HL-60 cells were plated at 1.2×10$^5$ cells/ml. Eighteen hours after plating, cells in duplicate were treated with the drug. Four days later, the cells were harvested, and a nitro blue tetrazolium reduction assay was performed (Collins et al, (1979); J. Exp. Med. 149:969-974). The percentage of differentiated cells was determined by counting a total of 200 cells and recording the number that contained intracellular black-blue formazan deposits. Verification of differentiation to monocytic cells was determined by measuring phagocytic activity.

In vitro Transcription Assay. Transcription activity was measured in ROS 17/2.8 bone cells that were stably transfected with a 24-hydroxylase ("24Ohase") gene promoter upstream of a luciferase reporter gene (Arbour et al, (1998)). Cells were given a range of doses. Sixteen hours after dosing, the cells were harvested and luciferase activities were measured using a luminometer. (RLU=relative luciferase units).

Intestinal Calcium Transport and Bone Calcium Mobilization. Male, weanling Sprague-Dawley rats were placed on a Diet 11 (0.47% Ca) diet+AEK for one week followed by Diet 11 (0.02% Ca)+AEK for 3 weeks. The rats were then switched to a diet containing 0.47% Ca for one week followed by two weeks on a diet containing 0.02% Ca. Administration of drug began during the last week on the 0.02% calcium diet. Four consecutive ip doses were given approximately 24 hours apart. 24 hours after the last dose, blood was collected from the severed neck, and the concentration of serum calcium was determined as a measure of bone calcium mobilization. The first 10 cm of the intestine was also collected for intestinal calcium transport analysis using the everted gut sac method. The everted sac method was carried out as described in Sicinski et al, J. Med. Chem. 41, 4662-4674 (1998).

The negative control material ("vehicle") was prepared by volumetrically measuring ethanol (<5%) and propylene glycol, mixing and than placing in storage at 2-8° C.

Positive Control Material. 1.25(OH)$_2$D$_3$ was prepared by determining the concentration of an ethanol stock solution using UV spectrophotometry (extinction coefficient 18,200; λ$_{max}$=265 nm). The required amount of 1.25(OH)$_2$D$_3$ was volumetrically measured into propylene glycol so that there was less than 5% ethanol in the final solution. The solution was mixed and then stored at 2-8° C.

The instant vitamin D analogs were prepared by first determining the concentration of an ethanol stock solution using UV spectrophotometry (extinction coefficient 42,000, λ$_{max}$=252 nm). The analog solutions were than volumetrically added to propylene glycol so that there was less than 5% ethanol in the final solution. The solution was mixed and stored at 2-8° C.

Dose Administration Method. All experimental doses were administered by intraperitoneal injection in 100 microliters for 4-7 consecutive days spaced approximately 24 hours apart. 1.25(OH)$_2$D$_3$ was administered 4 consecutive days.

Serum Calcium Analysis. 24 hours after the final dose, approximately 1 ml of blood was allowed to coagulate at room temperature, and then centrifuged at 3000×g for 15 minutes. The serum was transferred to a polypropylene tube and stored frozen at −20° C. The level of calcium was determined by diluting the serum into 0.1% lanthum chloride. Absorbance was measured on an atomic absorption spectrophotometer, Perkin Elmer Model 3110 (Shelton, Conn.).

Example I

Preparation of (20R)-1α-hydroxy-2-[3'-hydroxypropylidene]-19,24,25,26,27-pentanorvitamin D$_3$ (8a). Referring to SCHEME I, the starting bicyclic aldehyde 1a was obtained according to the procedure set forth herein. (See Fall et al., Tetrahedron Lett. 43, 1433 (2002)).

(a) Wittig reaction of the aldehyde 1a. Benzoic acid (1R,3aR,4S,7aR)-7a-methyl-1-((R)-1-methyl-prop-2-enyl)-octahydro-inden-4-yl ester (2a). To the methyltriphenylphosphonium bromide (31 mg, 87 µmol) in anhydrous THF (0.5 mL) at 0° C. was added drop-wise n-BuLi (2.65 M in hexanes, 64 µL, 0.170 mmol) under argon with stirring. After 5 minutes, another portion of $Ph_3P^+CH_3\ Br^-$ was added (31 mg, 87 µmol), and the solution was stirred at 0° C. for 10 minutes, and then at room temperature for 20 minutes. The orange-red mixture was cooled to negative 78° C. and siphoned to a solution of aldehyde 1a (33 mg, 0.109 mmol) in anhydrous THF (0.1 mL). The reaction mixture was stirred at −78° C. and stopped by addition of brine cont. 1% HCl three hours after adding of the first portion of the Wittig reagent. Ethyl acetate (3 mL), benzene (2 mL), ether (1 mL), saturated $NaHCO_3$ (1 mL) and water (1 ml) were added, and the mixture was vigorously stirred at room temperature for 18 hours. Then, an organic phase was separated, washed with brine, dried ($MgSO_4$) and evaporated. The oily residue was filtered through a silica Sep-Pak (2 g). Elution with hexane/ethyl acetate (99:1) resulted in pure olefinic product 2a (19 mg, 68%). 2a: $[\alpha]^{24}_D$+71.0° (c 0.90 $CHCl_3$); $^1H$ NMR (400 MHz, $CDCl_3$) δ1.058 (3H, d, J=6.6 Hz, 21-$H_3$), 1.079 (3H, s, 18-$H_3$), 4.83 (1H, dd, J=10.1, 1.7 Hz, (23E)-H), 4.91 (1H, dd, J=17.2, 1.7 Hz, (23Z)-H), 5.41 (1H, narr m, 8α-H), 5.67 (1H, ddd, J=17.2, 10.1, 8.6 Hz, 22-H), 7.44 (2H, t, J=7.4 Hz, Ar—H), 7.55 (1H, t, J=7.4 Hz, Ar—H), 8.05 (2H, d, J=7.4 Hz, Ar—H); HRMS (ESI) exact mass calcd for $C_{17}H_{21}O_2$ ($M^+$−$C_6H_5CO$) 257.1542, measured 257.1530.

(b) Hydrogenation of 22-olefin 2a. Benzoic acid (1R,3aR,4S,7aR)-1-((R)-sec-butyl)-7a-methyl-octahydro-inden-4-yl ester (3a). To a solution of olefin 2a (45 mg, 0.146 mmol) in ethyl acetate (5.5 mL) was added Pd/C (10%, 27 mg), and the resultant suspension was stirred under constant flow of hydrogen at room temperature for 19 hours. Then, the suspension was filtered. The filtrate was evaporated and applied to silica Sep-Pak cartridge (2 g). Elution with hexane/ethyl acetate (96:4) gave pure, oily ester 3a (40 mg, 87%). 3a: $[\alpha]^{24}_D$+53.0° (c 0.58 $CHCl_3$); $^1H$ NMR (400 MHz, $CDCl_3$) δ 0.836 (3H, t, J=7.4 Hz, 23-$H_3$), 0.931 (3H, d, J=6.6 Hz, 21-$H_3$), 1.047 (3H, s, 18-H3), 5.41 (1H, narr m, 8α-H), 7.45 (2H, t, J=7.4 Hz, Ar—H), 7.55 (1H, t, J=7.4 Hz, Ar—H), 8.06 (2H, d, J=7.4 Hz, Ar—H).

(c) Hydrolysis of the benzoate 3a. (1R,3aR,4S,7aR)-1-((R)-sec-Butyl)-7a-methyl-octahydro-inden-4-ol (4a). Solution of the ester 3a (40 mg, 0.129 mmol) in 10% methanolic KOH (2 mL) was heated at 50° C. for 24 hours, poured into water and extracted using ethyl acetate. The organic phase was washed with $NaHCO_3$ and water, and then dried ($MgSO_4$) and evaporated. The oily residue was purified using silica Sep-Pak (2 g). Elution with hexane/ethyl acetate (96:4) resulted in pure product 4a (22 mg, 81%). 4a: $[\alpha]^{24}_D$+38° (c 1.0 $CHCl_3$); $^1H$ NMR (400 MHz, $CDCl_3$) δ 0.824 (3H, t, J=7.4 Hz, 23-$H_3$), 0.821 (3H, d, J=6.5 Hz, 21-$H_3$), 0.931 (3H, s, 18-$H_3$), 4.08 (1H, narr m, 8αH); HRMS (ESI) exact mass calcd for $C_{14}H_{26}O$ ($M^+$) 210.1984, measured 210.1990.

(d) Oxidation of alcohol 4a. (1R,3aR,4S,7aR)-1-((R)-sec-Butyl)-7a-methyl-octahydro-inden-4-one (5a). A solution of NMO (23 mg) and molecular sieves 4 Å (138 mg) in methylene chloride (0.9 mL) was stirred at room temperature for 15 minutes. The solution of 4a (21 mg, 0.10 mmol) in methylene chloride (0.15 mL) was added followed by TPAP (2.5 mg). The resultant dark mixture was stirred for 30 minutes and applied to a silica Sep-Pak (2 g). Elution using hexane/ethyl acetate (95:5) produced pure ketone 5a (18.5 mg, 88%).

5a: $[\alpha]^{24}_D$−11° (c 0.78 $CHCl_3$); $^1H$ NMR (400 MHz, $CDCl_3$) δ 0.640 (3H, s, 18-$H_3$), 0.843 (3H, t, J=7.4 Hz, 23-$H_3$), 0.945 (3H, d, J=5.9 Hz, 21-$H_3$), 2.12 (1H, br d, J=12.8 Hz, 9β-H), 2.45 (1H, dd, J=11.6, 7.6 Hz, 14α-H); HRMS (ESI) exact mass calcd for $C_{14}H_{24}O$ ($M^+$) 208.1827, measured 208.1830.

(e) Wittig-Horner coupling of the ketone 5a with the phosphine oxide 6. 1α-[(tert-Butyldimethylsilyl)oxy]-2-[3'-[((tert-butyldimethylsilyl)oxy)propylidene]-19,24,25,26,27-pentanorvitamin $D_3$ tert-Butyldimethylsilyl Ether (E-isomer, 7a). To a solution of phosphine oxide 6 (11.5 mg, 15.6 µmol) in anhydrous THF (0.30 mL) at −78° C., phenyllithium (1.8 M in butyl ether, 9 µL, 16 µmol) was slowly added under argon with stirring. The solution turned deep orange. The mixture was stirred at −78° C. for 20 minutes. A pre-cooled (−78° C.) solution of ketone 5a (19 mg, 91 µmol) in anhydrous THF (0.10 mL) was slowly added. The mixture was stirred under argon at −78° C. for 2 hours and at 6° C for 16 hours. Ethyl acetate and water were added, and the organic phase was washed with brine, dried with $MgSO_4$, and evaporated. The residue was dissolved in hexane, applied on a silica column, and washed with hexane/ethyl acetate (98.5:1.5) to produce silylated vitamin 7a (1.44 mg, 13%). The column was then washed with hexane/ethyl acetate (95:5) to recover a portion of unchanged C,D-ring ketone 5a (7 mg), and hexane/ethyl acetate (6:4) was used to recover diphenylphosphine oxide 6 (4.2 mg). 7a: $^1H$ NMR (400 MHz, $CDCl_3$) δ −0.023, 0.051, 0.050, 0.059 and 0.069 (3H, 3H, 3H, 3H and 6H, each s, 6×Si$CH_3$), 0.549 (3H, s, 18-$H_3$), 0.819, 0.896 and 0.923 (each 9H, each s, 3×Si-t-Bu), 2.33 (2H, m, =CH—$CH_2$), 2.79 (1H, dd, J~12.5, 3 Hz, 9β-H), 3.05 (1H, dd, J=12.5, 4.4 Hz, 10β-H), 3.62 (2H, m, $CH_2$—$CH_2$—O), 4.34 (1H, m, w/2=21 Hz, 1β-H), 4.81 (1H, narr m, 3α-H), 5.47 (1H, t, J=7.5 Hz, =CH—$CH_2$), 5.87 and 6.11 (1H and 1H, each d, J=10.9 Hz, 7- and 6-H); HRMS (ESI) exact mass calcd for $C_{43}H_{82}O_3Si_3Na$ ($M^+$+Na) 753.5470, fd 753.5465.

(f) Hydrolysis of the silyl protecting groups in the 19-norvitamin D derivative 7a. 1α-Hydroxy-2-[3'-hydroxypropylidene]-19,24,25,26,27-pentanorvitamin $D_3$ (E-isomer, 8a). To a solution of the protected vitamin 7a (1.4 mg, 1.91 µmol) in anhydrous THF (1.3 mL), tetrabutylammonium fluoride (1.0 M in THF, 86 µL, 86 µmol) and triethylamine (16 µL) were added. The mixture was stirred under argon at room temperature for 18 hours, poured into brine and extracted using ethyl acetate and diethyl ether. Organic extracts were washed with brine, dried using $MgSO_4$, and evaporated. The residue was purified using HPLC (9.4 mm×25 cm Zorbax-Sil column, 4 mL/min) using hexane/2-propanol (8:2) solvent system. Pure 19-norvitamin 8a (0.56 mg, 72%) was collected at $R_V$ 25.5 mL. In a reversed-phase HPLC (9.4 mm×25 cm Eclipse XDB-C18 column, 4 mL/min) using methanol/water (9:1) solvent system, vitamin 8a was collected at $R_V$ 42 mL. 8a ("RBH"): UV (in EtOH) $\lambda_{max}$ 243.0, 251.5, 261.5 nm; $^1H$ NMR (400 MHz, $CDCl_3$) δ 0.549 (3H, s, 18-$H_3$), 0.917 (3H, br d, J=5.5 Hz, 21-$H_3$), 0.837 (3H, t, J=7.4 Hz, 23-$H_3$), 2.47 (2H, narr m, 4α- and 4β-H), 2.36 and 2.54 (1H and 1H, each m, =CH—$CH_2$), 2.82 (1H, dm, J~13.5 Hz, 9β-H), 3.16 (1H, dd, J=13.2, 5.0 Hz, 10β-H), 3.66 and 3.76 (1H and 1H, each m, $CH_2$—$CH_2$—O), 4.44 (1H, m, w/2=20 Hz, 1β-H), 4.85 (1H, narr m, 3α-H), 5.67 (1H, t, J=7.5 Hz, =CH—$CH_2$), 5.88 and 6.31 (1H and 1H, each d, J=11.6 Hz, 7- and 6-H); HRMS (ESI) $C_{25}H_{40}O_3Na$ ($M^+$+Na) 411.3079, measured 411.3086.

Example II

Preparation of (20S)-1α-hydroxy-2-[3'-hydroxypropylidene]-19,24,25,26,27-pentanorvitamin $D_3$ (8b). As set forth in SCHEME II, starting bicyclic aldehyde 2b was obtained according to the procedure set forth in Granja et al., J. Org. Chem. 58, 124 (1993).

(a) Wittig reaction of the aldehyde 2b. Benzoic acid (1R,3aR,4S,7aR)-7a-methyl-1-((S)-1-methyl-prop-2-enyl)-octahydro-inden-4-yl ester (2b). To methyltriphenylphosphonium bromide (63 mg, 0.179 mmol) in anhydrous THF (0.5 mL) at 0° C., n-BuLi (2.65 M in hexanes, 128 μL, 0.340 mmol) was added drop-wise under argon with stirring. After 5 minutes, another portion of $Ph_3P^+CH_3$ $Br^-$ was added (63 mg, 0.179 mmol), and the solution was stirred at 0° C. for 10 minutes and at room temperature for 20 minutes. The orange-red mixture was cooled to negative 78° C. and siphoned to produce a solution of aldehyde 1b (56 mg, 0.185 mmol) in anhydrous THF (0.2 mL). The reaction mixture was stirred at −78° C. and stopped by adding brine cont. 1% HCl three hours after addition of the first portion of the Wittig reagent. Ethyl acetate (3 mL), benzene (2 mL), ether (1 mL), saturated $NaHCO_3$ (1 mL), and water (1 ml) were added, and the mixture was vigorously stirred at room temperature for 18 hours. An organic phase was separated, washed with brine, dried with $MgSO_4$, and evaporated. The oily residue was filtered through a silica Sep-Pak (2g). Elution using hexane/ethyl acetate (98:2) resulted in pure olefinic product 2b (46 mg, 73%). 2b: $[\alpha]^{24}_D$+12° (c 0.39 $CHCl_3$); $^1H$ NMR (400 MHz, $CDCl_3$) δ 0.940 (3H, d, J=6.6 Hz, 21-$H_3$), 1.046 (3H, s, 18-$H_3$), 4.87 (1H, dd, J=10.1, 1.6 Hz, (23E)-H), 4.97 (1H, dd, J=17.1, 1.6 Hz, (23Z)-H), 5.41 (1H, narr m, 8α-H), 5.70 (1H, dt, J=17.1, 9.7 Hz, 22-H), 7.44 (2H, t, J=7.3 Hz, Ar—H), 7.55 (1H, t, J=7.3 Hz, Ar—H), 8.05 (2H, d, J=7.3 Hz, Ar—H; HRMS (ESI) exact mass calcd for $C_{17}H_{21}O_2$ $C_{17}H_{21}O_2$ ($M^+$−$C_6H_5CO$) 257.1542, measured 257.1533.

(b) Hydrogenation of 22-olefin 2b. Benzoic acid (1R,3aR,4S,7aR)-1-((S)-sec-butyl)-7a-methyl-octahydro-inden-4-yl ester (3b). To a solution of olefin 2b (47 mg, 0.153 mmol) in ethyl acetate (5.7 mL), Pd/C (10%, 28 mg) was added, and the resultant suspension was stirred under constant flow of hydrogen at room temperature for 20 hours. The suspension was filtered. The filtrate was evaporated and applied to silica Sep-Pak cartridge (2g). Elution using hexane/ethyl acetate (97:3) produced pure, oily ester 3b (40.5 mg, 86%). 3b: $[\alpha]^{24}_D$+49.0° (c 0.37 $CHCl_3$); $^1H$ NMR (400 MHz, $CDCl_3$ δ), 0.829 (3H, d, J=6.6 Hz, 21-$H_3$), 0.850 (3H, t, J=7.4 Hz, 23-$H_3$), 1.045 (3H, s, 18-$H_3$), 5.41 (1H, narr m, 8α-H), 7.44 (2H, t, J=7.6 Hz, Ar—H), 7.55 (1H, tt, J=7.4, ~1.4 Hz, Ar—H), 8.06 (2H, m, Ar—H).

(c) Hydrolysis of the benzoate 3b. (1R,3aR,4S,7aR)-1-((S)-sec-Butyl)-7a-methyl-octahydro-inden-4-ol (4b). Solution of the ester 3b (40.5 mg, 0.131 mmol) in 10% methanolic KOH (2 mL) was heated at 50° C. for 23 hours, poured into water and extracted using ethyl acetate. The organic phase was washed using $NaHCO_3$ and water, dried using $MgSO_4$, and evaporated. The oily residue was purified using silica Sep-Pak (2 g). Elution using hexane/ethyl acetate (97:3) produced pure product 4b (22 mg, 80%). 4b: $[\alpha]^{24}_D$+25° (c 0.29 $CHCl_3$); $^1H$ NMR (400 MHz, $CDCl_3$) δ 0.822 (3H, t, J=7.6 Hz, 23-$H_3$), 0.813 (3H, d, J=7.3 Hz, 21-$H_3$), 0.929 (3H, s, 18-$H_3$), 4.07 (1H, narr m, 8α-H); HRMS (ESI) exact mass calcd for $C_{14}H_{26}O$ ($M^+$) 210.1984, measured 210.1984.

(d) Oxidation of alcohol 4b. (1R,3aR,4S,7aR)-1-((S)-sec-Butyl)-7a-methyl-octahydro-inden-4-one (5b). A solution of NMO (28 mg) and molecular sieves 4 Å (145 mg) in methylene chloride (0.9 mL) was stirred at room temperature for 15 minutes. The solution of 4b (22 mg, 0.104 mmol) in methylene chloride (0.15 mL) was added followed by TPAP (3.0 mg). The resultant dark mixture was stirred for 30 minutes, and applied to a silica Sep-Pak (2 g). Elution with hexane/ethyl acetate (96:4) produced pure ketone 5b (18.0 mg, 82%). 5b: $[\alpha]^{24}_D$−27.5° (c 0.8 $CHCl_3$); $^1H$ NMR (400 MHz, $CDCl_3$) δ 0.636 (3H, s, 18-$H_3$), 0.857 (3H, t, J=7.4 Hz, 23-$H_3$), 0.848 (3H, d, J~7 Hz, 21-$H_3$), 2.09 (1H, br d, J=12.0 Hz, 9β-H), 2.45 (1H, dd, J=11.5, 7.6 Hz, 14α-H); HRMS (ESI) exact mass calcd for $C_{14}H_{24}O$ ($M^+$) 208.1827, measured 208.1836.

(e) Wittig-Horner coupling of the ketone 5b with the phosphine oxide 6. (20S)-1α-[(tert-Butyldimethylsilyl)oxy]-2-[3'-[((tert-butyldimethylsilyl)oxy)propylidene]-19,24,25,26,27-pentanorvitamin $D_3$ tert-Butyldimethylsilyl Ether (E-isomer, 7b). To a solution of phosphine oxide 6 (11.5 mg, 15.6 μmol) in anhydrous THF (0.30 mL) at −78° C., phenyllithium (1.8 M in butyl ether, 9 μL, 16 μmol) was slowly added under argon with stirring. The solution turned deep orange. The mixture was stirred at −78° C. for 20 minutes. A pre-cooled (−78 ° C.) solution of the ketone 5b (19 mg, 91 μmol) in anhydrous THF (0.10 mL) was slowly added. The mixture was stirred under argon at −78° C. for 2 hours and at 6° C. for 16 hours. Ethyl acetate and water were added. The organic phase was washed with brine, dried using $MgSO_4$, and evaporated. The residue was dissolved in hexane, applied on a silica column and washed using hexane/ethyl acetate (98.5:1.5) producing silylated vitamin 7b (2.2 mg, 19%). The column was washed using hexane/ethyl acetate (96:4) to recover a portion of unchanged C,D-ring ketone 5b (9 mg), and hexane/ethyl acetate (6:4) was used to recover diphenylphosphine oxide 6 (4 mg). 7b: UV (in hexane) $\lambda_{max}$ 243.5, 252.5, 262.0 nm; $^1H$ NMR (400 MHz, $CDCl_3$) δ −0.023, 0.055, 0.059, and 0.069 (3H, 3H, 6H, and 6H, each s, 6× $SiCH_3$), 0.552 (3H, s, 18-$H_3$), 0.819, 0.896, and 0.923 (each 9H, each s, 333 Si-t-Bu), 2.36 and 2.54 (1H and 1H, each m, =CH—$CH_2$), 2.79 (1H, br d, J~12.7 Hz, 9β-H), 3.05 (1H, dd, J~12., 5.0 Hz, 10β-H), 3.63(2H, m, $CH_2$—$CH_2$—O), 4.34 (1H, m, w/2=21 Hz, 1β-H), 4.81 (1H, narr m, 3α-H), 5.47 (1H, t, J=7.5 Hz, HC=C—$C_2$), 5.85 and 6.13 (1H and 1H, each d, J=11.6 Hz, 7- and 6-H); HRMS (ESI) exact mass calculated for $C_{43}H_{82}O_3Si_3Na$ ($M^+$+Na) 753.5470, measured 753.5462.

(f) Hydrolysis of the silyl protecting groups in the 19-norvitamin D derivative 7b. (20S)-1α-Hydroxy-2-[3'-hydroxypropylidene]-19,24,25,26,27-pentanorvitamin $D_3$ (E-isomer, 8b). To a solution of the protected vitamin 7b (2.2 mg, 3.01 μmol) in anhydrous THF (2 mL), tetrabutylammonium fluoride (1.0 M in THF, 135 μL, 135 μmol) and triethylamine (25 μL) were added. The mixture was stirred under argon at room temperature for 18 hours, poured into brine and extracted using ethyl acetate and diethyl ether. Organic extracts were washed using brine, dried using $MgSO_4$, and evaporated. The residue was purified using HPLC (9.4 mm×25 cm Zorbax-Sil column, 4 mL/min) using hexane/2-propanol (8:2) solvent system. Pure 19-norvitamin 8b (0.66 mg, 53%) was collected at $R_V$ 25.5 mL. In reversed-phase HPLC (9.4 mm×25 cm Eclipse XDB-C18 column, 4 mL/min) using methanol/water (95:5) solvent system, vitamin 8b was collected at $R_V$ 42 mL. 8b ("SBH"): UV (in EtOH) $\lambda_{max}$ 243.0, 251.5, 261.5 nm; $^1H$ NMR (400 MHz, $CDCl_3$) δ 0.545 (3H, s, 18-$H_3$), 0.835 (3H, d, J=5.8 Hz, 21-$H_3$), 0.836 (3H, t, J=7.3 Hz, 23-$H_3$), 2.47 (2H, narr m, 4α- and 4β-H), 2.36 and 2.54 (1H and 1H, each m, =CH—$CH_2$), 2.82 (1H, br d, J=12.9 Hz, 9β-H), 3.16 (1H, dd, J=13.2, 5.0 Hz, 10β-H), 3.66 and 3.76 (1H and 1H, each m, $CH_2$—$CH_2$—O), 4.45 (1H, m, w/2=20 Hz, 1β-H), 4.85 (1H, narr m, 3α-H), 5.67 (1H, t, J=7.5 Hz, =CH—$CH_2$), 5.88 and 6.31 (1H and 1H, each d, J=11.6 Hz, 7- and 6-H); HRMS (ESI) exact mass calcd for $C_{25}H_{40}O_3Na$ (M$^+$+Na) 411.3079, measured 411.3089.

Example III

Preparation of (20R)-1α-hydroxy-2-[3'-hydroxypropylidene]-19,23,24-trinorvitamin $D_3$ (15a) and (20S)-1α-hydroxy-2-[3'-hydroxypropylidene]-19,23,24-trinorvitamin $D_3$ (15b).

(a) Conversion of aldehyde 1a into 22-nitrile 9. Benzoic acid-(1R,3aR,4S,7aR)-1-((R-cyano-methyl-methyl)-7a-methyl-octahydro-inden-4-yl ester (9). To a solution of a benzoyloxy aldehyde 1a (284 mg, 0.90 mmol) in anhydrous pyridine (5 mL), $NH_2OH \times HCl$ (210 mg) was added. The mixture was stirred at room temperature for 20 hours. The mixture was poured into water and extracted using ethyl acetate. The combined organic phases were separated, washed using saturated $NaHCO_3$ solution, water, and saturated $CuSO_4$ solution, dried using $MgSO_4$, and evaporated. The oily residue was purified using column chromatography on silica gel. Elution using hexane/ethyl acetate (9:1) produced pure (less polar) E-oxime (167 mg) and (more) polar Z-oxime (105 mg, total yield 89%). E-oxime: $^1$H NMR (400 MHz, CDCl$_3$) δ 1.09 (3H, d, J=6.7 Hz, 18-H$_3$), 1.14 (3H, s, 21-H$_3$), 2.40 (1H, m, 20-H), 5.42 (1H, narr m, 8α-H), 7.27 (1H, d, J=8.0 Hz, 22-H), 7.45 (2H, t, J~7 Hz, Ar—H), 7.56 (1H, t, J=7.4 Hz, Ar—H), 8.04 (2H, d, J=7.4 Hz, Ar—H). Z-oxime: $^1$H NMR (400 MHz, CDCl$_3$) δ 1.09 (3H, d, J=6.7 Hz, 18-H$_3$), 1.13 (3H, s, 21-H$_3$), 3.28 (1H, m, 20-H), 5.42 (1H, narr m, 8α-H), 6.25 (1H, d, J=8.1 Hz, 22-H), 7.45 (2H, t, J~7 Hz, Ar—H), 7.56 (1H, t, J=7.3 Hz, Ar—H), 8.04 (2H, d, J=7.3 Hz, Ar—H).

The solution of oximes (both isomers, 248 mg, 0.75 mmol) in acetic anhydride (8 mL) was refluxed for 1.5 hours. The reaction mixture was cooled, poured carefully on ice and extracted using toluene. Extracts were combined, washed with water, $NaHCO_3$ and brine, dried using $MgSO_4$, and evaporated. The residue was applied to silica Sep-Pak (5 g). Elution with hexane/ethyl acetate (95:5) produced pure semi-crystalline nitrile 9 (212 mg, 91%). 9: $[\alpha]^{24}_D$+81.5° (c 0.9 CHCl$_3$); $^1$H NMR (400 MHz, CDCl$_3$) δ 1.124 (3H, s, 18-H$_3$), 1.373 (3H, d, J=7.1 Hz, 21-H$_3$), 1.90 (1H, br d, J=12.8 Hz, 9β-H), 2.68 (1H, pentet, J=7.0 Hz, 20-H), 5.43 (1H, narr m, 8α-H), 7.45 (2H, t, J=7.6 Hz, Ar—H), 7.57 (1H, t, J=7.5 Hz, Ar—H), 8.03 (2H, d, J=7.4 Hz, Ar—H); HRMS (ESI) exact mass calcd for $C_{13}H_{20}ON$ (M$^+$–$C_6H_5CO$) 206.1545, measured 206.1539.

(b) Alkylation of the nitrile 9 with iso-butyl bromide. Benzoic acid-(1S,3aR,4S,7aR)-1-((S)-1-cyano-1,3-dimethyl-butyl)-7a-methyl-octahydro-inden-4-yl ester (10). n-BuLi (2.65 M in hexanes, 103 µL, 0.272 mmol) was added at 0° C. to the flask containing diisopropylamine (42 µL, 0.272 mmol) and THF (0.4 mL). The solution was stirred at 0° C. for 20 minutes, cooled to negative 78° C. and siphoned to produce a solution of 9 (77 mg, 0.248 mmol) in THF (0.3 mL). The resultant yellow mixture was stirred for 30 minutes. HMPA (100 µL) was added. Stirring continued for another 15 minutes. (CH$_3$)$_2$CHCH$_2$Br (68 µL, 0.62 mmol) was added. The solution was allowed to warm up to –40° C. over a duration of 1 hour. Saturated $NH_4Cl$ was added. The mixture was extracted using ethyl acetate. The combined organic phases were washed with water, dried using $MgSO_4$, and evaporated. The residue was applied to silica SepPak (2 g). Elution using hexane/ethyl acetate (98:2) resulted in pure semi-crystalline 10 (60 mg, 66%; 74% based on recovered substrate); further elution with hexane/ethyl acetate (97:3) gave un-reacted 9 (8.5 mg). 10: $[\alpha]^{24}_D$+66.5° (c 1.15 CHCl$_3$); $^1$H NMR (400 MHz, CDCl$_3$) δ 1.055 and 0.971 (3H and 3H, each d, J=6.6 Hz, 24- and 25-H$_3$), 1.369 (3H, s, 18-H$_3$), 1.456 (3H, s, 21-H$_3$), 2.15 (1H, br d, J=12.7 Hz, 9β-H), 5.40 (1H, narr m, 8α-H), 7.45 (2H, t, J~7 Hz, Ar—H), 7.57 (1H, t, J=7.4 Hz, Ar—H), 8.04 (2H, d, J=7.4 Hz, Ar—H); HRMS (ESI) exact mass calculated for $C_{24}H_{33}O_2N$ (M$^+$) 367.2511, measured 367.2518.

(c) Hydrolysis of the 8β-benzoyloxy group in the nitrile 10. (S)-2-((1S,3aR,4S,7aR)-4-hydroxy-7a-methyl-octahydro-inden-1-yl)-2,4-dimethyl-pentanenitrile (11). Benzoyloxy nitrile 10 (90 mg, 0.246 mmol) was treated using 10% methanolic KOH (4 mL) at 50° C. for 18 hours. After concentration under vacuum, the reaction mixture was poured into water and extracted using benzene and ether. The organic extracts were combined, washed with brine, dried using $MgSO_4$, and evaporated. The residue was re-dissolved in hexane/ethyl acetate (95:5). The solution was passed through a silica gel Sep-Pak cartridge. Evaporation of solvents produced hydroxy nitrile 11 (66 mg, 92%). 11: $[\alpha]^{24}_D$+28° (c 0.29 CHCl$_3$); $^1$H NMR (400 MHz, CDCl$_3$) δ 1.043 and 0.959 (3H and 3H, 2×d, J=6.6 Hz, 24-H$_3$ and 25-H$_3$), 1.236 (3H, s, 18-H$_3$), 1.410 (3H, s, 21-H$_3$), 2.08 (1H, d m, J=12.4 Hz, 9β-H), 4.09 (1H, narr m, 8α-H), HRMS (ESI) exact mass calcd for $C_{17}H_{29}ON$ (M$^+$) 263.2249, measured 263.2254.

(d) Reductive decyanation of hydroxy nitrile 11. (1R,3aR,4S,7aR)-1-((R)-1,3-Dimethyl-butyl)- and (1R,3aR,4S,7aR)-1-((S)-1,3-Dimethyl-butyl)-7a-methyl-octahydro-inden-4-ol (12a,b). A solution of nitrile 11 (49 mg, 0.186 mmol) in t-BuOH (50 µL) and ether (0.20 mL) was added drop-wise at 0° C., under argon, to a blue solution of potassium (55 mg, 1.4 mmol) in HMPA (0.17 mL) and ether (0.42 mL). A cooling bath was removed, and stirring continued for 4 hours at room temperature under argon. The reaction mixture was diluted using benzene. Un-reacted potassium was removed and, a few drops of 2-propanol were added. The organic phase was washed using water, dried using $MgSO_4$, and evaporated. The residue was applied to a silica Sep-Pak (2 g). Elution using hexane/ethyl acetate (95:5) produced a 1:1 mixture of epimeric alcohols 12a and 12b (37 mg, 84%). 12a and 12b: $^1$H NMR (400 MHz, CDCl$_3$, selected signals) δ 0.932 (s, 18-H$_3$ in 12b), 0.944 (s, 18-H$_3$ in 12a), 2.01 (br d, J=12.7 Hz, 9β-H from both isomers), 4.07 (narr m, 8α-H from both isomers); HRMS (ESI) exact mass calculated for $C_{16}H_{30}O$ (M$^+$) 238.2297, measured 238.2294.

(e) Oxidation of alcohols 12a and 12b. (1R,3aR,7aR)-1-((R)-1,3-dimethyl-butyl)- and (1R,3aR,7aR)-1-((S)-1,3-dimethyl-butyl)-7a-methyl-octahydro-inden-4-one (13a and 13b). The solution of NMO (23 mg) and molecular sieves 4 Å (123 mg) in methylene chloride (0.9 mL) was stirred at room temperature for 15 minutes. The solution of 12a and 12b (20.5 mg, 86 µmol) in methylene chloride (0.15 mL) was added followed by the TPAP (2.5 mg). The resultant dark mixture was stirred for 30 minutes, diluted with methylene chloride, and filtered through silica SepPak (2 g). Elution using methylene chloride produced a 1:1 mixture of epimeric ketones 13a and 13b (21 mg, 91%). Separation of isomers was achieved using HPLC (9.4 mm×25 cm Zorbax-Sil column, 4 mL/min) using hexane/ethyl acetate (95:5) solvent system. The 20S ketone 13b was collected at $R_V$ 39 mL and the R-isomer 13a at $R_V$ 40 mL. 13a: $[\alpha]^{24}_D$+11° (c 0.28 CHCl$_3$); $^1$H NMR (400 MHz, CDCl$_3$) δ 0.653 (3H, s, 18-H$_3$), 0.816 and 0.881 (3H and 3H, each d, J=6.6 Hz, 24- and 25-H$_3$), 0.922 (3H, d, J=5.9 Hz, 21-H$_3$), 2.14 (1H, br d, J=12.4 Hz, 9β-H), 2.44 (1H, dd, J=11.6, 7.6 Hz, 14α-H); HRMS (ESI) exact mass calcd for $C_{16}H_{28}O$ (M$^+$) 236.2140, measured 236.2135.

13b: $[\alpha]^{24}_D$ –48° (c 0.28 CHCl$_3$); $^1$H NMR (400 MHz, CDCl$_3$) δ 0.641(3H, s, 18-H$_3$), 0.827 and 0.831 (3H and 3H, each d, J=6.6 Hz, 24- and 25-H$_3$), 0.894 (3H, d, J=5.9 Hz, 21-H$_3$), 2.12 (1H, br d, J=12.7 Hz, 9β-H), 2.44 (1H, dd, J=11.5, 7.6 Hz, 14α-H); HRMS (ESI) exact mass calculated for C$_{16}$H$_{28}$O (M$^+$) 236.2140, measured 236.2135.

(f) Wittig-Horner coupling of the ketones 13a,b with the phosphine oxide 6. (a) 1α-[(tert-Butyldimethylsilyl)oxy]-2-[3'-[((tert-butyldimethylsilyl)oxy)propylidene]-19,23,24-trinorvitamin D$_3$ tert-Butyldimethylsilyl Ether (E-isomer, 14a). To a solution of phosphine oxide 6 (28 mg, 38 µmol) in anhydrous THF (0.40 mL) at –78° C., phenyllithium (1.8 M in butyl ether, 22 µL, 39 µmol) was slowly added under argon with stirring. The solution turned deep orange. The mixture was stirred at –78° C. for 20 minutes, and a pre-cooled (–78° C.) solution of the ketone 13a (7.5 mg, 32 µmol) in anhydrous THF (0.10 mL) was slowly added. The mixture was stirred under argon at –78° C. for 2 hours and at 6° C. for 16 hours. Ethyl acetate and water were added, and the organic phase was washed using brine, dried using MgSO$_4$, and evaporated. The residue was dissolved in hexane, applied on a silica Sep-Pak cartridge, and eluted using hexane/ethyl acetate (95.5:0.5) to produce 19-norvitamin derivative 14a (12 mg, 50%). The Sep-Pak was washed using hexane/ethyl acetate (98:2) to recover a portion of unchanged C,D-ring ketone 13a (1 mg), and with hexane/ethyl acetate (6:4) to recover diphenylphosphine oxide 6 (3 mg). 14a: $^1$H NMR (400 MHz, CDCl$_3$) δ –0.023, 0.052, 0.056, 0.059 0.062 and 0.069 (each 3H, each s, 6×SiCH$_3$), 0.567 (3H, s, 18-H$_3$), 0.818, 0.897, and 0.923 (each 9H, each s, 3×Si-t-Bu) 2.37 (2H, each m, =CH—CH$_2$), 2.79 (1H, br d, J=12.5 Hz, 9β-H), 3.05 (1H, dd, J=12.4, 4.4 Hz, 10β-H), 3.62 (2H, each m, CH$_2$—CH$_2$—O), 4.34 (1H, m, w/2=20 Hz, 1β-H), 4.80 (1H, narr m, 3α-H), 5.47 (1H, t, J~7 Hz, =CH—CH$_2$), 5.87 and 6.11 (1H and 1H, each d, J=11.1 Hz, 7- and 6-H).

(b) (20S)-1α-[(tert-Butyldimethylsilyl)oxy]-2-[3'-[((tert-butyldimethylsilyl)oxy) propylidene]-19,23,24-trinorvitamin D$_3$ tert-Butyldimethylsilyl Ether (E-isomer, 14b). To a solution of phosphine oxide 6 (27.5 mg, 37 µmol) in anhydrous THF (0.40 mL) at –78° C., phenyllithium (1.8 M in butyl ether, 21 µL, 38 µmol) was slowly added under argon with stirring. The solution turned deep orange. The mixture was stirred at –78° C. for 20 minutes, and a pre-cooled (–78° C.) solution of the ketone 13b (7.0 mg, 30 µmol) in anhydrous THF (0.10 mL) was slowly added. The mixture was stirred under argon at –78° C. for 2 hours and at 6° C. for 16 hours. Ethyl acetate and water were added, and the organic phase was washed using brine, dried using MgSO$_4$, and evaporated. The residue was dissolved in hexane, applied to a silica Sep-Pak cartridge, and eluted using hexane/ethyl acetate (95.5:0.5) to produce 19-norvitamin derivative 14b (12 mg, 53%). The Sep-Pak was then washed using hexane/ethyl acetate (98:2) to recover a portion of unchanged C,D-ring ketone 13b (1 mg), and with hexane/ethyl acetate (6:4) to recover diphenylphosphine oxide 6 (2 mg). 14b: $^1$H NMR (400 MHz, CDCl$_3$) δ–0.023, 0.056, 0.060, 0.071 and 0.088 (3H, 3H, 6H, 3H and 3H, each s, 6× SiCH$_3$), 0.551 (3H, s, 18-H$_3$), 0.819, 0.897, and 0.924 (each 9H, each s, 3× Si-t-Bu), 2.33 (2H, each m, =CH—CH$_2$), 2.79 (1H, br d, J=12.4 Hz, 9β-H), 3.04 (1H, dd, J=12.4, 4.4 Hz, 10β-H), 3.62 (2H, each m, CH$_2$—CH$_2$—O), 4.34 (1H, m, w/2=20 Hz, 11β-H), 4.81 (1H, narr m, 3α-H), 5.47 (1H, t, J~7 Hz, =HC—CH$_2$), 5.87 and 6.12 (1H and 1H, each d, J=11.1 Hz, 7- and 6-H).

(g) Hydrolysis of the silyl protecting groups in the 19-norvitamin D derivatives 14a,b. (a) (20R)-1α-Hydroxy-2-[3'-hydroxypropylidene]-19,23,24-trinorvitamin D$_3$ (E-isomer, 15a). To a solution of the protected vitamin 14a (11.5 mg, 15 µmol) in anhydrous THF (9.5 mL), tetrabutylammonium fluoride (1.0 M in THF, 450 µL, 450 µmol) and triethylamine (84 µL) were added. The mixture was stirred under argon at room temperature for 18 hours, poured into brine, and extracted using ethyl acetate and diethyl ether. Organic extracts were washed using brine, dried using MgSO$_4$, and evaporated. The residue was purified using HPLC (9.4 mm×25 cm Zorbax-Sil column, 4 mL/min) using hexane/2-propanol (7:3) solvent system. Pure 1.9-norvitamin 15a (6.2 mg, 98%) was collected at R$_V$ 24 mL. In reversed-phase HPLC (9.4 mm×25 cm Eclipse XDB-C18 column, 4 mL/min) using methanol/water (95:5) solvent system, vitamin 15a was collected at R$_V$ 31.5 mL. 15a ("HPBR"): UV (in EtOH) $\lambda_{max}$ 243.0, 251.0, 261.0 nm; $^1$H NMR (400 MHz, CDCl$_3$) δ 0.600 (3H, s, 18-H$_3$), 0.894 (3H, d, J=6.0 Hz, 21-H$_3$), 0.820 and 0 879 (1H and 1H, each d, J=6.4 Hz, 24- and 25-H$_3$), 2.44 (2H, narr m, 4α and 4β-H), 2.31 and 2.52 (1H and 1H, each m, =CH—CH$_2$), 2.81 (1H, br d, J=12.7 Hz, 9β-H), 3.15 (1H, dd, J=13.0, 4.8 Hz, 10β-H), 3.65 and 3.74 (1H and 1H, each m, CH$_2$—CH$_2$—O), 4.41 (1H, m, w/2=20 Hz, 1β-H), 4.82 (1H, narr m, 3α-H), 5.62 (1H, t, J=7.3 Hz, HC=C—CH$_2$), 5.88 and 6.30 (1H and 1H, each d, J=11.2 Hz, 7- and 6-H); HRMS (ESI) exact mass calculated for C$_{27}$H44O$_3$Na (M$^+$+Na) 439.3188, measured 439.3177.

(b) (20S)-1α-Hydroxy-2-[3'-hydroxypropylidene]-19,23,24-trinorvitamin D$_3$ (E-isomer, 15b). To a solution of the protected vitamin 14b (11.5 mg, 15 µmol) in anhydrous THF (9.5 mL), tetrabutylammonium fluoride (1.0 M in THF, 450 µL, 450 µmol) and triethylamine (84 µL) were added. The mixture was stirred under argon at room temperature for 18 hours, poured into brine, and extracted using ethyl acetate and diethyl ether. Organic extracts were washed using brine, dried using MgSO$_4$, and evaporated. The residue was purified using HPLC (9.4 mm×25 cm Zorbax-Sil column, 4 mL/min) using hexane/2-propanol (7:3) solvent system. Pure 19-norvitamin 15b (6.2 mg, 98%) was collected at R$_V$ 24 mL. In reversed-phase HPLC (9.4 mm×25 cm Eclipse XDB-C18 column, 4 mL/min) using methanol/water (95:5) solvent system, vitamin 15b was collected at R$_V$ 30 mL. 15b ("HPBS"): UV (in EtOH.)$\lambda_{max}$ 243.0, 251.0, 261.0 nm; $^1$H NMR (400 MHz, CDCl$_3$) δ 0.546 (3H, s, 18-H$_3$), 0.879 (3H, d, J=6.5 Hz, 21-H$_3$), 0.815 and 0 824 (3H and 3H, each d, J=6.2 Hz and J=6.3 Hz, 24- and 25-H$_3$), 2.46 (2H, narr m, 4α- and 4β-H), 2.33 and 2.54 (1H and 1H, each m, =CH—CH$_2$), 2.81 (1H, br d, J=12.7 Hz, 9β-H), 3.15 (1H, dd, J=13.0, 4.8 Hz, 10β-H), 3.67 and 3.73 (1H and 1H, each m, CH$_2$—CH$_2$—O), 4.42 (1H, m, w/2=20 Hz, 1β-H), 4.84 (1H, narr m, 3α-H), 5.65 (1H, t, J=7.3 Hz, =CH—CH$_2$), 5.88 and 6.30 (1H and 1H, each d, J=11.2 Hz, 7- and 6-H); HRMS (ESI) exact mass calculated for C$_{27}$H$_{44}$O$_3$Na (M$^+$+Na) 439.3188, measured 439.3180.

SCHEME I and SCHEME II are set forth below.
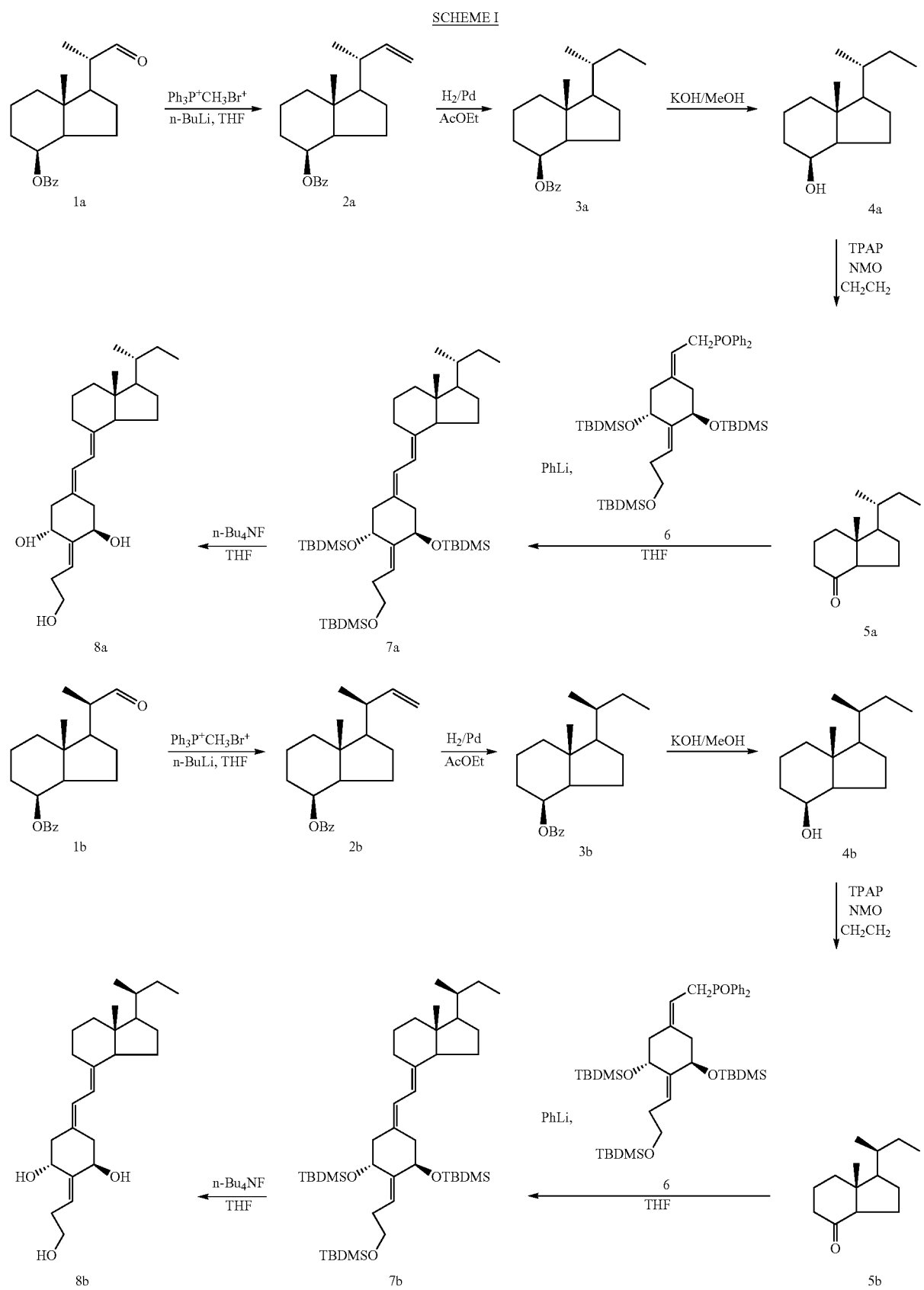

SCHEME II
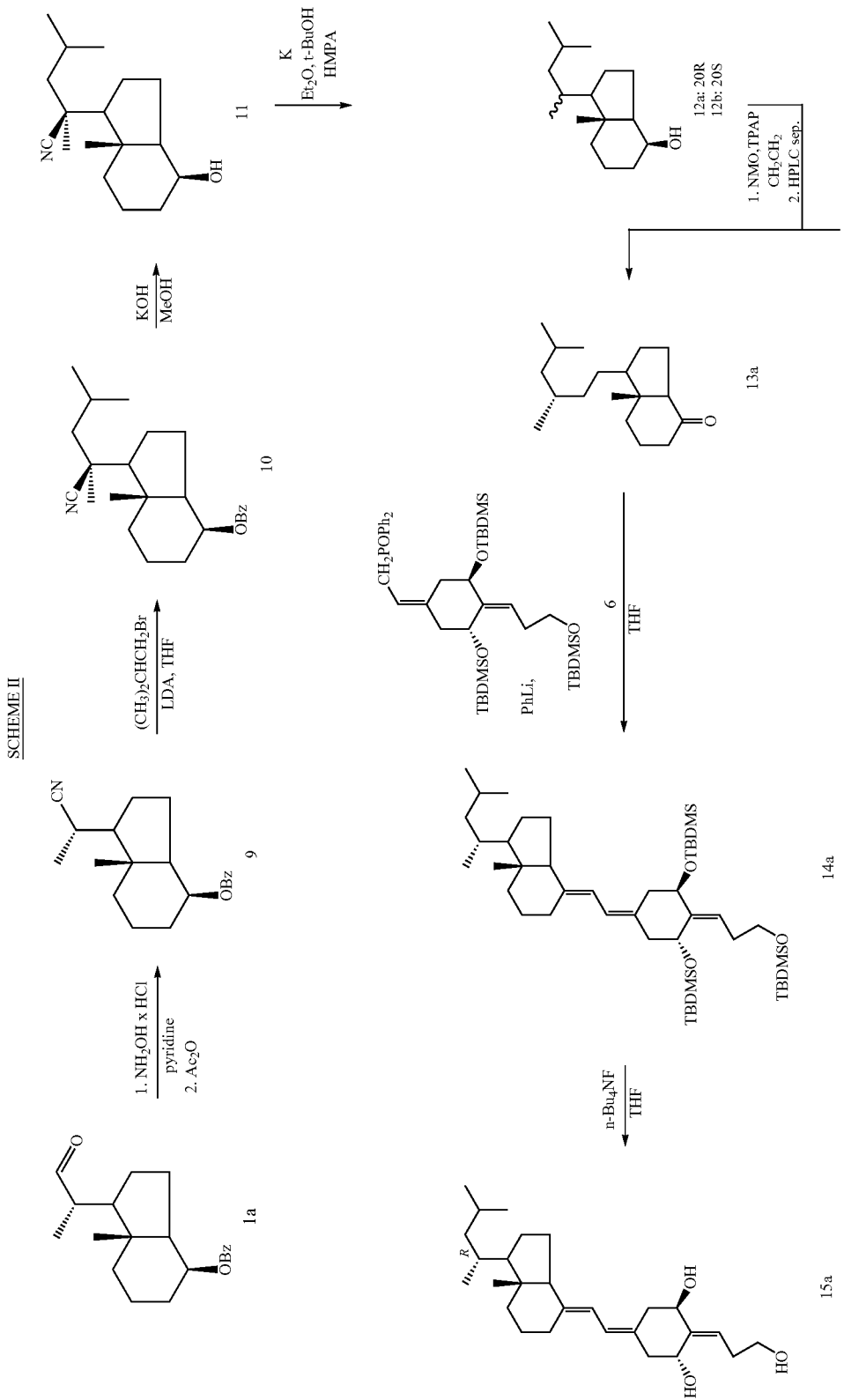

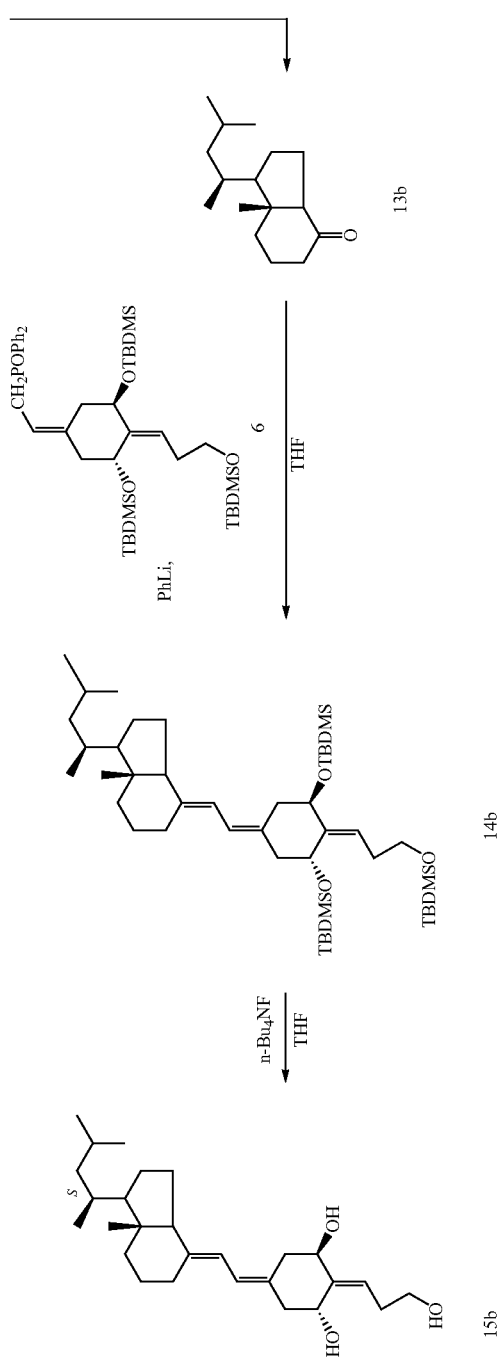

We claim:

1. A compound of the formula:

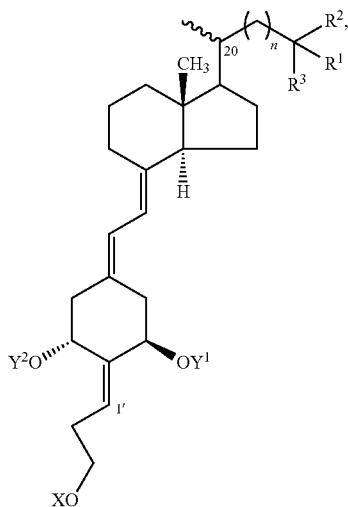

wherein the solid line to C(1') provides that the compound is an E- or Z-geometrical isomer respecting the 2-propylidene segment, wherein the C(20) is the stereochemical center, wherein the ⌇⌇⌇ provides an R or S configuration, wherein n is 1 or 2, wherein $Y^1$ is a member selected from the group consisting of hydrogen, deuterium and a first hydroxy-protecting group, wherein $Y^2$ is a member selected from the group consisting of hydrogen, deuterium and a second hydroxy-protecting group, wherein X is a third hydroxy-protecting group, wherein $R^1$ is a member selected from the group consisting of hydrogen, deuterium and methyl, wherein $R^2$ is a member selected from the group Consisting of hydrogen, deuterium and methyl, wherein $R^3$ is a member selected from the group consisting of hydrogen, deuterium and methyl and wherein ⌇⌇⌇ is a member selected from the group consisting of ⋯⋯ and ▬▬, and esters thereof.

2. The compound of claim 1 wherein X is a member selected from the group consisting of hydrogen, deuterium, $C_{1-10}$ branched or straight alkyl, $C_{1-10}$ branched or straight alkyl substituted with one or more hydroxy groups, $C_{1-10}$ branched or straight alkyl substituted with one or more $C_{1-10}$ branched or straight alkoxy groups, $C_{1-10}$ branched or straight alkyl substituted with one or more aryloxy groups, carbonyl substituted with one or more $C_{1-10}$ branched or straight alkoxy groups, $C_{1-6}$ branched or straight alkanoyl, $C_{1-6}$ branched or straight carboxyalkanoyl, aromatic acyl, silyl substituted with one or more $C_{1-10}$ branched or straight alkyl groups, silyl substituted with one or more $C_{1-10}$ branched or straight alkyl groups and silyl substituted with one or more aryl groups.

3. The compound of claim 2, wherein the carbonyl substituted with a $C_{1-10}$ branched or straight alkoxy groups is a member selected from the group consisting of methoxycarbonyl, ethoxycarbonyl, propoxycarhonyl, iso-propoxycarbonyl, butoxycarbonyl, isobutoxycarbonyl, tert-butoxycarbonyl, benzyloxycarbonyl and allyloxycarbonyl.

4. The compound of claim 2, wherein the $C_{1-6}$ branched or straight carboxyalkanoyl is a member selected from the group consisting of oxalyl, malonyl, succinyl and glutaryl and wherein the aromatic acyl is a member selected from the group consisting of benzoyl, halo-substituted benzoyl, nitro-substituted benzoyl and $C_{1-10}$ straight or branched alkyl substituted benzoyl.

5. The compound of claim 2, wherein the $C_{1-10}$ branched or straight alkyl substituted with one or more $C_{1-10}$ branched or straight alkoxy groups is a member selected from the group consisting of methoxymethyl, ethoxymethyl, methoxyethoxymethyl, tetrahydrofuranyl and tetrahydropyranyl.

6. The compound of claim 2, wherein the silyl substituted with one or more $C_{1-10}$ branched or straight alkyl groups is a member selected from the group consisting of trimethylsilyl, triethylsilyl, t-butyldimethylsilyl and dibutylmethylsilyl and wherein the silyl substituted with one or more aryl groups is a member selected from the group consisting of diphenymethylsilyl, phenyldimethylsilyl and diphenyl-t-butylsilyl.

7. The compound of claim 2, wherein the $C_{1-10}$ branched or straight alkyl substituted with one or more aryloxy groups is a member selected from the group consisting of phenyl-substituted phenyl, $C_{1-10}$ straight or branched alkyl-substituted phenyl, nitro-substituted phenyl and halo-substituted phenyl.

8. The compound of claim 1, wherein the compound is an E-geometrical isomer.

9. The compound of claim 1, wherein the compound is a Z-geometrical isomer.

10. The compound of claim 6, wherein X is t-butyldimethylsilyl.

11. The compound of claim 10. wherein $Y_1$ is t-butyldimethylsilyl.

12. The compound of claim 11, wherein $Y^2$ is t-butyldimethylsilyl.

13. The compound of claim 1, wherein X is hydrogen.

14. The compound of claim 13, wherein $Y^1$ is hydrogen.

15. The compound of claim 14, wherein $Y^2$ is hydrogen.

16. The compound of claim 1, wherein n is 1, wherein $R^1$ and $R^2$ are methyl, and wherein $R^3$ is hydrogen.

17. An E-isomer of (20R)-1α-hydroxy-2-(3'-hydroxypropylidene)-19,24,25,26,27-penta-nor-vitamin $D_3$.

18. An E-isomer of (20S)-1α-hydroxy-2-(3'-hydroxypropylidene)-19,24,25,26,27-penta-nor-vitamin $D_3$.

19. An E-isomer of (20R)-1α-hydroxy-2-(3'-hydroxypropylidene)-19,23,24-tri-nor-vitamin $D_3$.

20. An E-isomer of (20S)-1α-hydroxy-2-(3'-hydroxypropylidene)-19,23,24-tri-nor-vitamin $D_3$.

21. A method of making a hydrindanone intermediate compound for use in making the compound of claim 1, wherein n is 1, wherein $R^1$, $R^2$, and $R^3$ are each hydrogen and wherein ⌇⌇⌇ is ▬▬,, comprising:

providing a starting compound of the formula:

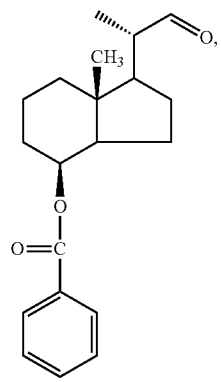

reacting the starting compound with a ylide reactant to produce an alkene-containing product, hydrogenating the alkene-containing product to produce an oily ester product, hydrolysing, the oily ester product to produce an alcohol product and oxidizing the alcohol product to produce the hydrindanone intermediate compound having the formula:

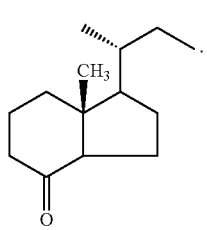

22. A method of making the compound of claim 1, wherein n is 1, wherein $R^1$, $R^2$, and $R^3$ are each hydrogen and wherein ⁓is ◀, comprising:

coupling a hydrindanone intermediate compound having the formula,

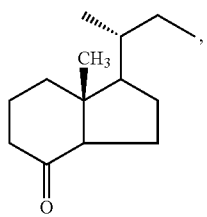

with lithium phosohinoxy carbanion to produce a coupled product having the protecting groups and hydrolyzing the protecting groups.

23. A method of making a hydrindanone intermediate compound for use in making the compound of claim 1, wherein n is 1, wherein $R^1$, $R^2$, and $R^3$ are each hydrogen and wherein ⁓is ◀, comprising:

providing a starting compound of the formula:

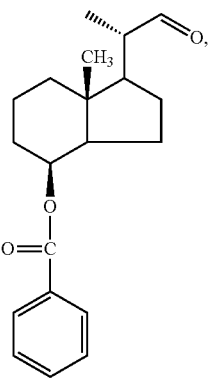

reacting the starting compound with a ylide reactant to produce an alkene-containing product, hydrogenating the alkene-containing product to produce an oily ester product, hydrolysing the oily ester product to produce an alcohol product and oxidizing the alcohol product to produce the hydrindanone intermediate compound having the formula:

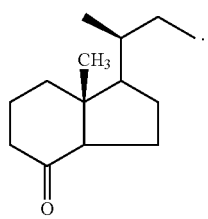

24. A method of making the compound of claim 1, wherein n is 1, wherein $R^1$, $R^2$, and $R^3$ are each hydrogen and wherein ⁓is ◀,comprising:

coupling a hydrindanone intermediate compound having the formula,

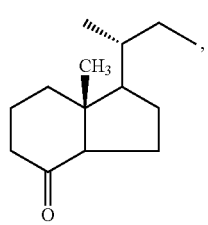

with lithium phosohinoxy carbanion to produce a coupled product having the protecting groups and hydrolyzing the protecting groups.

25. A method of making the compound of claim 1, wherein at least one of $R^1$, $R^2$ or $R^3$ is a methyl and wherein ⁓is ◀, comprising:

providing a starting compound of the formula:

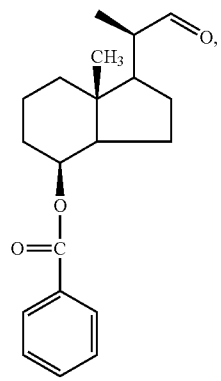

wherein ▬ is a member selected from the group consisting of ⁞⁞⁞⁞and ◂▬,,
converting the starting compound into a nitrile compound,
alkylating the nitrile compound with a first reactant of the formula:

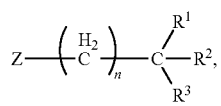

wherein n is an integer from 1 to 2, wherein Z is a member selected from the group consisting of Br, Cl and I and wherein at least one of $R^1$, $R^2$ or $R^3$ is a methyl to produce an alkylated nitrile product,
hydrolysing the alkylated nitrile product to produce a hydroxy nitrile product,
reductively decyanating the hydroxy nitrile product to produce a mixture of epimeric alcohol products,
oxidizing the mixture of epimeric alcohol products to produce a mixture of a 20S-ketone product and a 20R-ketone product,
separating the 20S-ketone and 20R-ketone products,
coupling the 20R-ketone product with lithium phosphinoxy carbanion to produce a coupled 20R product having the protecting groups and
hydrolyzing the protecting groups.

26. The method of claim 25, wherein n is 1, wherein Z is Br, wherein $R^1$ and $R^2$ are methyl, and wherein $R^3$ is hydrogen.

27. A method of making the compound of claim 1, wherein at least one of $R^1$, $R^2$ or $R^3$ is a methyl and wherein ∿ is ◂▬,, comprising:

providing a starting compound of the formula:

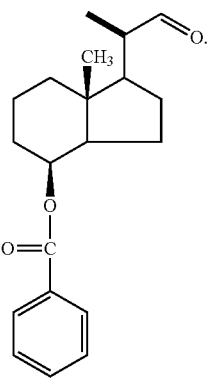

wherein ▬ is a member selected from the group consisting of ⁞⁞⁞⁞and ◂▬,,
converting the starting compound into a nitrite compound,
alkylating the nitrite compound with a first reactant of the formula:

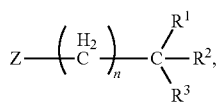

wherein n is 1 or 2, wherein Z is a member selected from the group consisting of Br, Cl and I and wherein at least one of $R^1$, $R^2$ or $R^3$ is a methyl, to produce an alkylated nitrile product,
hydrolysing the alkylated nitrile product to produce a hydroxy nitrite product,
reductively decyanating the hydroxy nitrite product to produce a mixture of epimeric alcohol products,
oxidizing the mixture of epimeric alcohol products to produce a mixture of a 20S ketone product and a 20R-ketone product,
separating the 20S-ketone and 20R-ketone products,
coupling the 20S-ketone product with lithium phosphinoxy carbanion to produce a coupled 20S product having the protecting groups and
hydrolysing the protecting groups.

28. The method of claim 27, wherein n is 1, wherein Z is Br, wherein $R^1$ and $R^2$ are methyl, and wherein $R^3$ is hydrogen.

\* \* \* \* \*